US010334933B2

(12) United States Patent
Decaux et al.

(10) Patent No.: US 10,334,933 B2
(45) Date of Patent: Jul. 2, 2019

(54) APPLICATOR AND CAPSULE FOR SUCH APPLICATOR

(71) Applicant: InDerm, Paris (FR)

(72) Inventors: Stéphane Decaux, Paris (FR); Géraldine Decaux, Paris (FR); Florent Simon, Filinges (FR)

(73) Assignee: InDerm (FR)

( * ) Notice: Subject to any disclaimer, the term of this patent is extended or adjusted under 35 U.S.C. 154(b) by 733 days.

(21) Appl. No.: 14/652,167

(22) PCT Filed: Dec. 16, 2013

(86) PCT No.: PCT/EP2013/076776
§ 371 (c)(1),
(2) Date: Jun. 15, 2015

(87) PCT Pub. No.: WO2014/091035
PCT Pub. Date: Jun. 19, 2014

(65) Prior Publication Data
US 2015/0327653 A1     Nov. 19, 2015

(30) Foreign Application Priority Data

Dec. 15, 2012   (FR) .................................. 12 03433
Dec. 17, 2012   (FR) .................................. 12 03445

(51) Int. Cl.
*A61H 7/00*       (2006.01)
*A61N 5/06*       (2006.01)
(Continued)

(52) U.S. Cl.
CPC ......... *A45D 34/041* (2013.01); *A45D 40/261* (2013.01); *A61H 7/003* (2013.01);
(Continued)

(58) Field of Classification Search
CPC ............... A45D 34/041; A45D 40/261; A45D 2200/055; A61N 5/0616; A61N 2005/063;
(Continued)

(56) References Cited

U.S. PATENT DOCUMENTS 7,896,908 B2 *   3/2011   Ripper ................. A61N 5/0616
                                                    606/9
8,262,592 B1 *   9/2012   Brooks ................ A45D 34/041
                                                    601/17
(Continued)

FOREIGN PATENT DOCUMENTS

JP      2010188058 A    9/2010
RU       2546493 C2     4/2015
WO     2010/111997 A2  10/2010

OTHER PUBLICATIONS

International Preliminary Report on Patentability dated Mar. 5, 2015, issued from corresponding PCT/EP2013/076776.

*Primary Examiner* — Sundhara M Ganesan
(74) *Attorney, Agent, or Firm* — Banner & Witcoff, Ltd.

(57) ABSTRACT

Applicator (1) and capsule (17) for such applicator. A capsule (17) for distributing, on a surface of a living body, a product containing an active component or forming a cosmetic product, the capsule having a product distribution zone and comprising: •—in a body, a supply of product which is in communication with the product distribution zone, and •—first linking means (150, 511*a*, 511*b*) for removably securing the capsule to second linking means of a housing (15) in which is disposed a light source (9).

34 Claims, 34 Drawing Sheets

(51) Int. Cl.
*A45D 34/04* (2006.01)
*A45D 40/26* (2006.01)
*A61H 15/00* (2006.01)
*A61H 15/02* (2006.01)
*A61M 35/00* (2006.01)
*A61M 37/00* (2006.01)

(52) U.S. Cl.
CPC ......... *A61H 15/0092* (2013.01); *A61H 15/02* (2013.01); *A61M 35/003* (2013.01); *A61N 5/0616* (2013.01); *A45D 2200/055* (2013.01); *A61H 2015/0064* (2013.01); *A61H 2201/0184* (2013.01); *A61H 2201/10* (2013.01); *A61H 2201/105* (2013.01); *A61H 2201/1246* (2013.01); *A61M 2037/0007* (2013.01); *A61N 2005/063* (2013.01); *A61N 2005/0631* (2013.01); *A61N 2005/0644* (2013.01); *A61N 2005/0659* (2013.01)

(58) Field of Classification Search
CPC .... A61N 2005/0659; A61N 2005/0644; A61H 15/0092; A61H 7/003; A61H 15/02; A61H 2201/0184; A61H 2015/0064; A61H 2201/10; A61H 2201/1246; A61H 2201/105; A61M 35/003; A61M 2037/0007

See application file for complete search history.

(56) References Cited

U.S. PATENT DOCUMENTS

| | | | |
|---|---|---|---|
| 8,356,952 B2 * | 1/2013 | Bennett | A45D 34/041 132/293 |
| 8,500,355 B2 * | 8/2013 | Liu | A45D 34/041 401/208 |
| 9,730,501 B2 * | 8/2017 | Diezinger | A45D 34/041 |
| 2006/0287616 A1 * | 12/2006 | Nan | A45D 34/041 601/17 |
| 2008/0014011 A1 | 1/2008 | Rossen | |
| 2008/0262394 A1 | 10/2008 | Pryor et al. | |
| 2009/0299236 A1 | 12/2009 | Pryor et al. | |
| 2011/0040235 A1 | 2/2011 | Castel | |
| 2011/0106067 A1 | 5/2011 | Geva et al. | |
| 2012/0207532 A1 | 8/2012 | Ho | |
| 2012/0238926 A1 * | 9/2012 | Diezinger | A45D 34/041 601/154 |

* cited by examiner

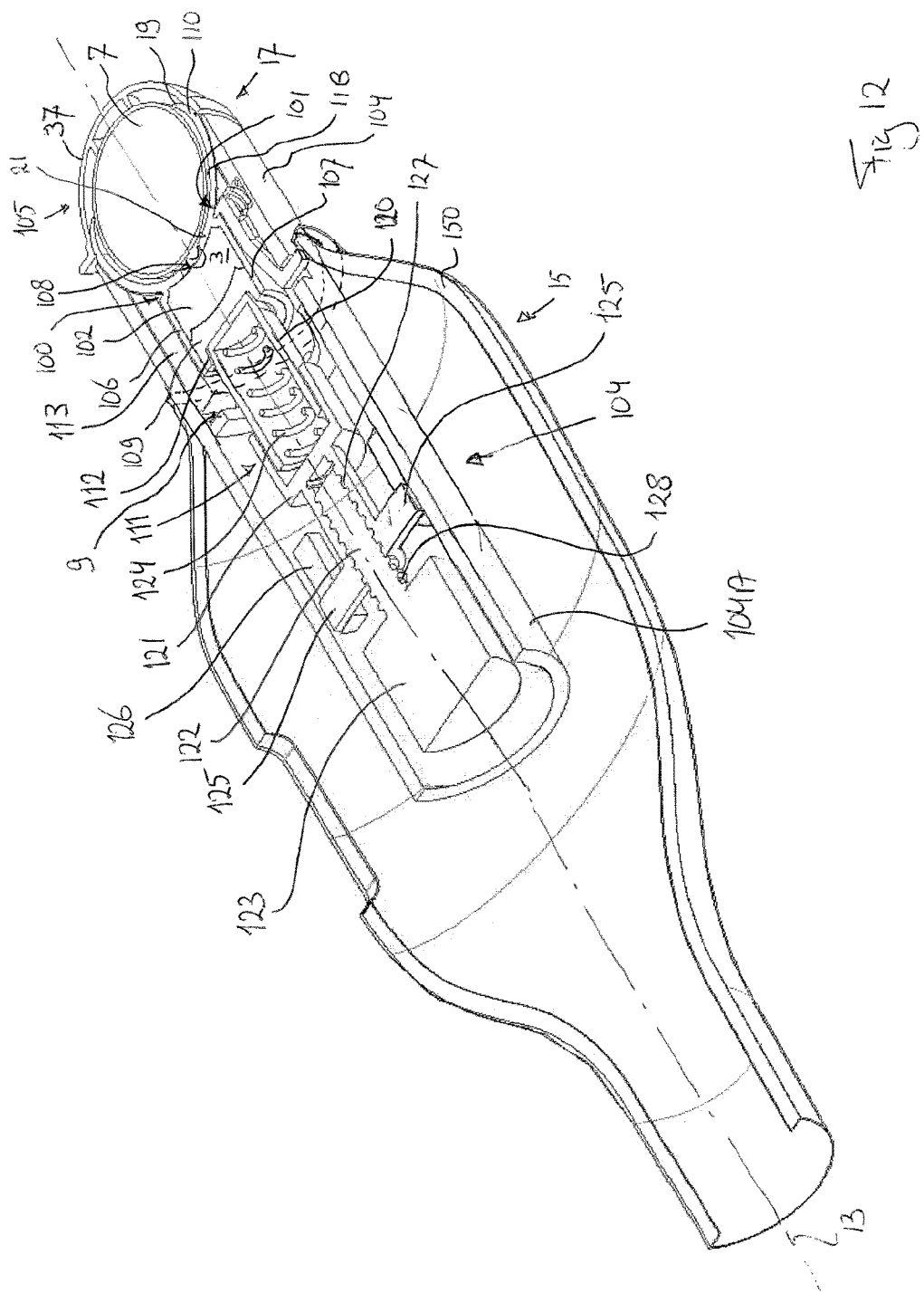

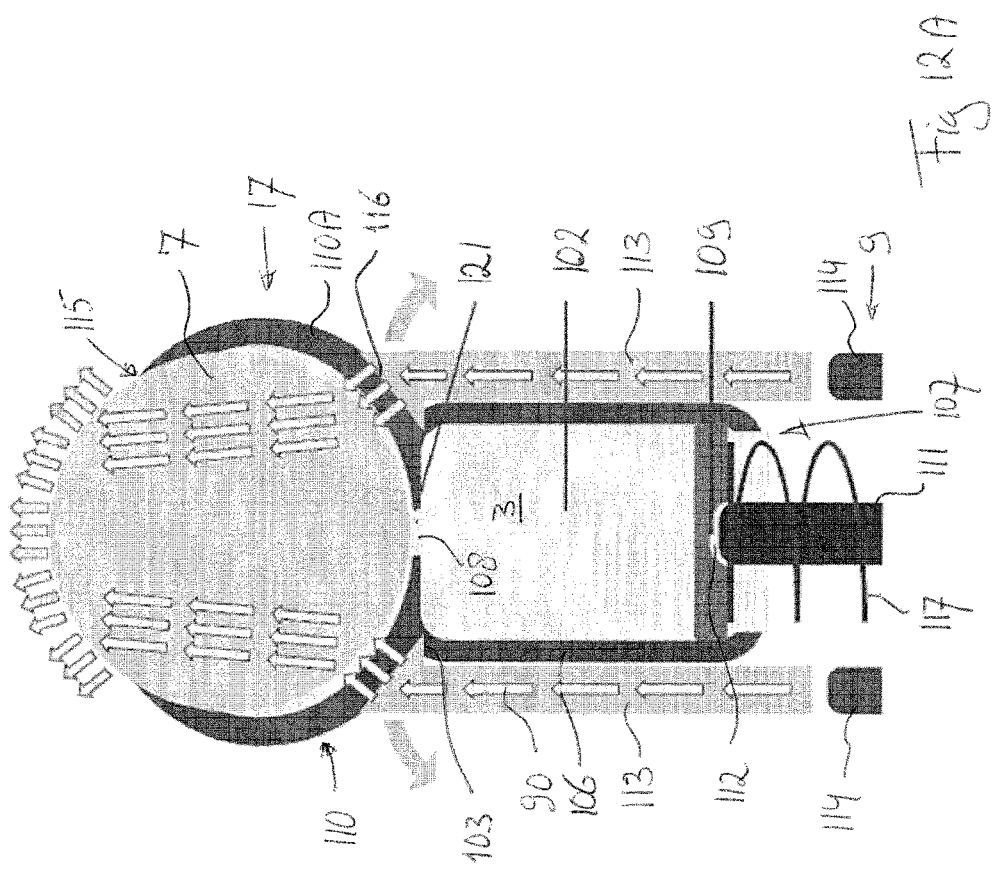

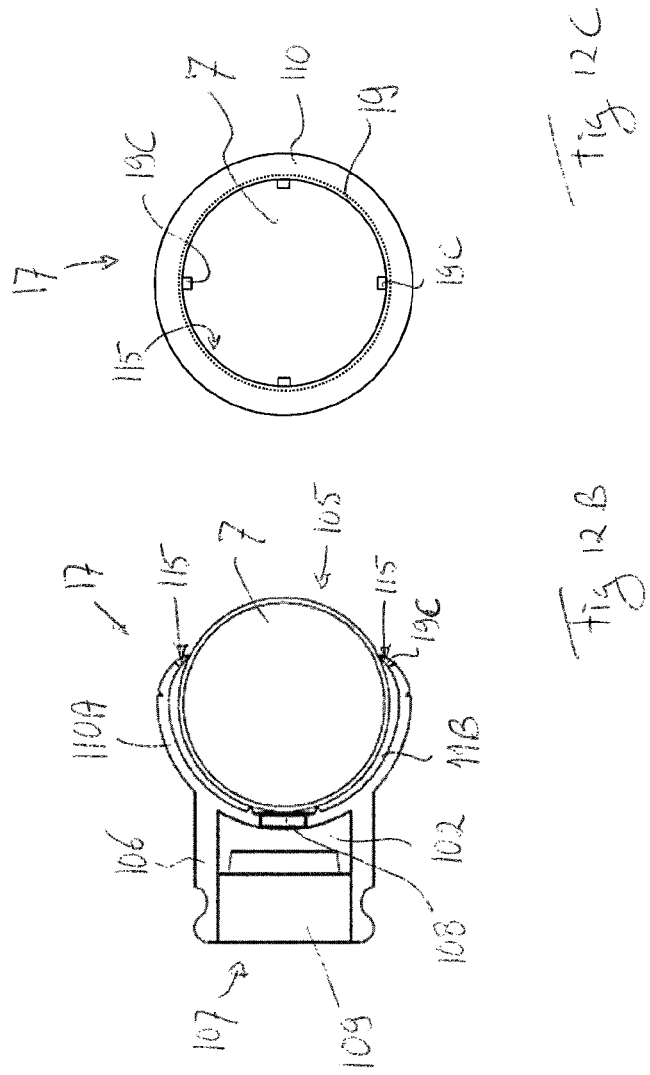

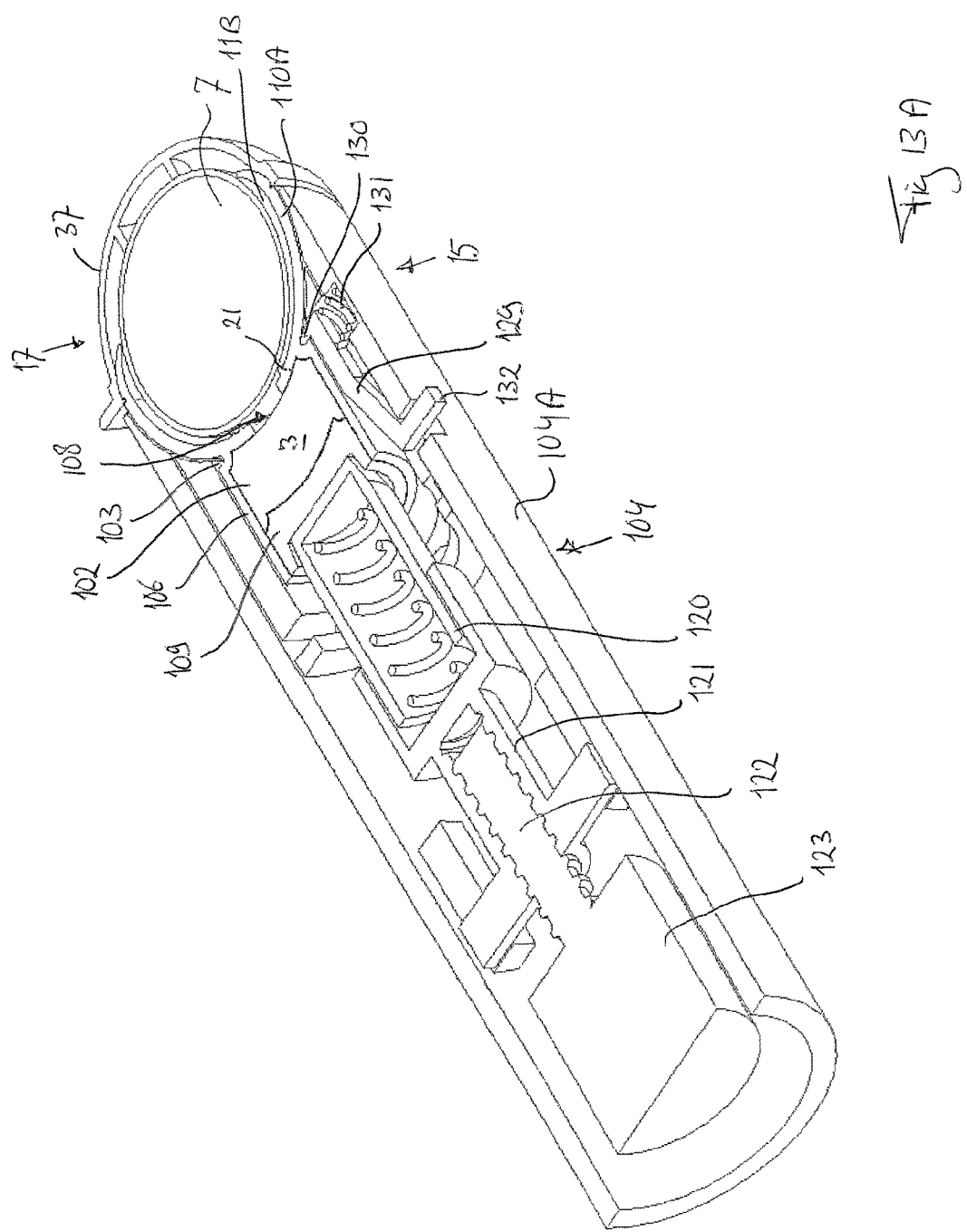

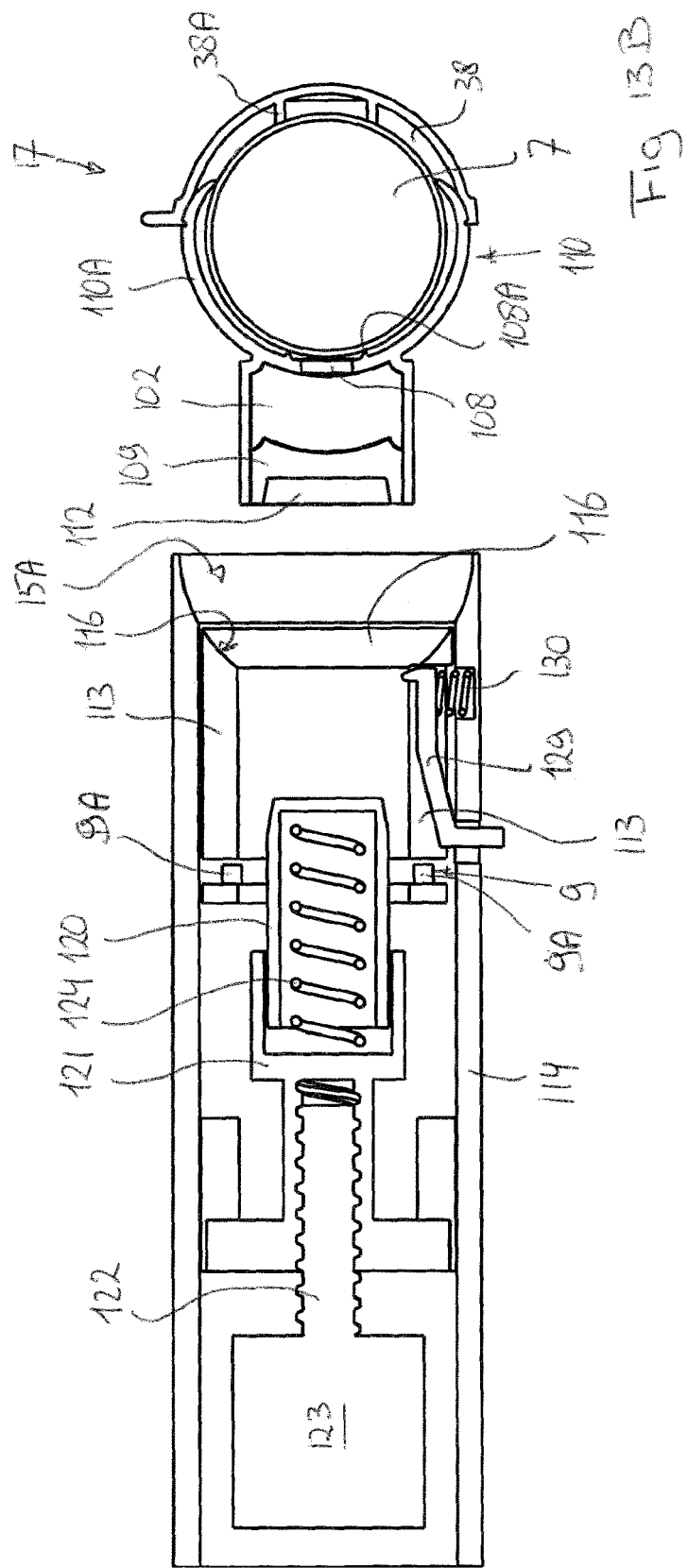

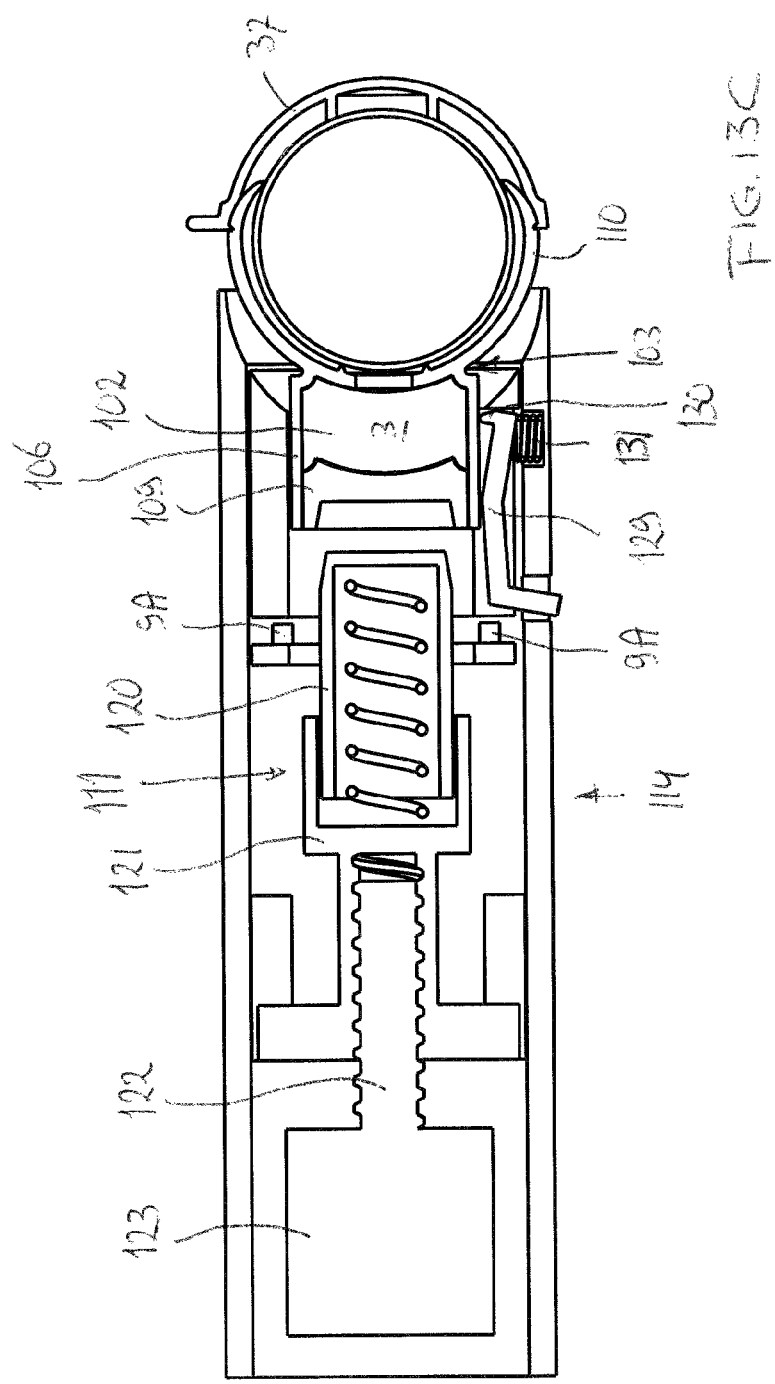

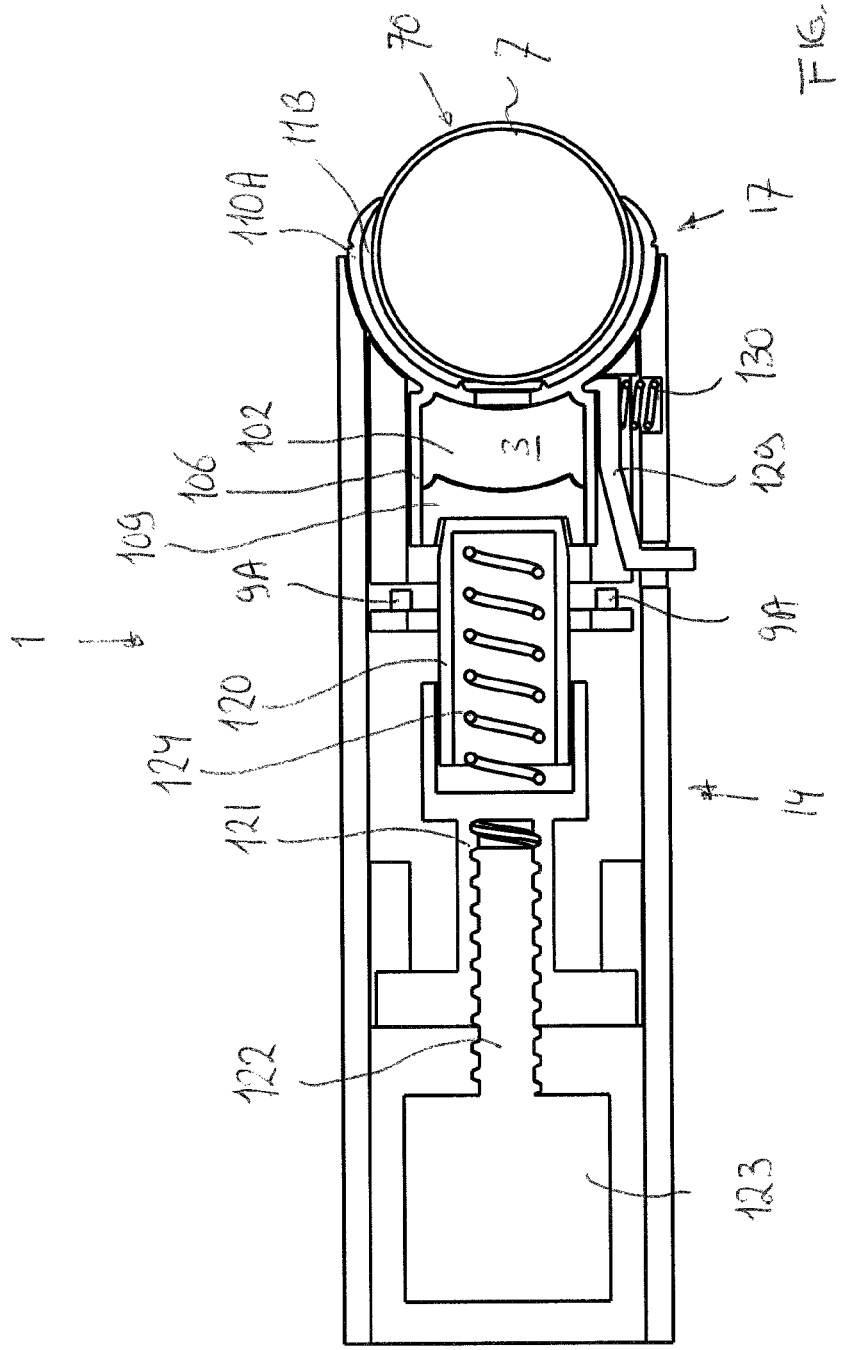

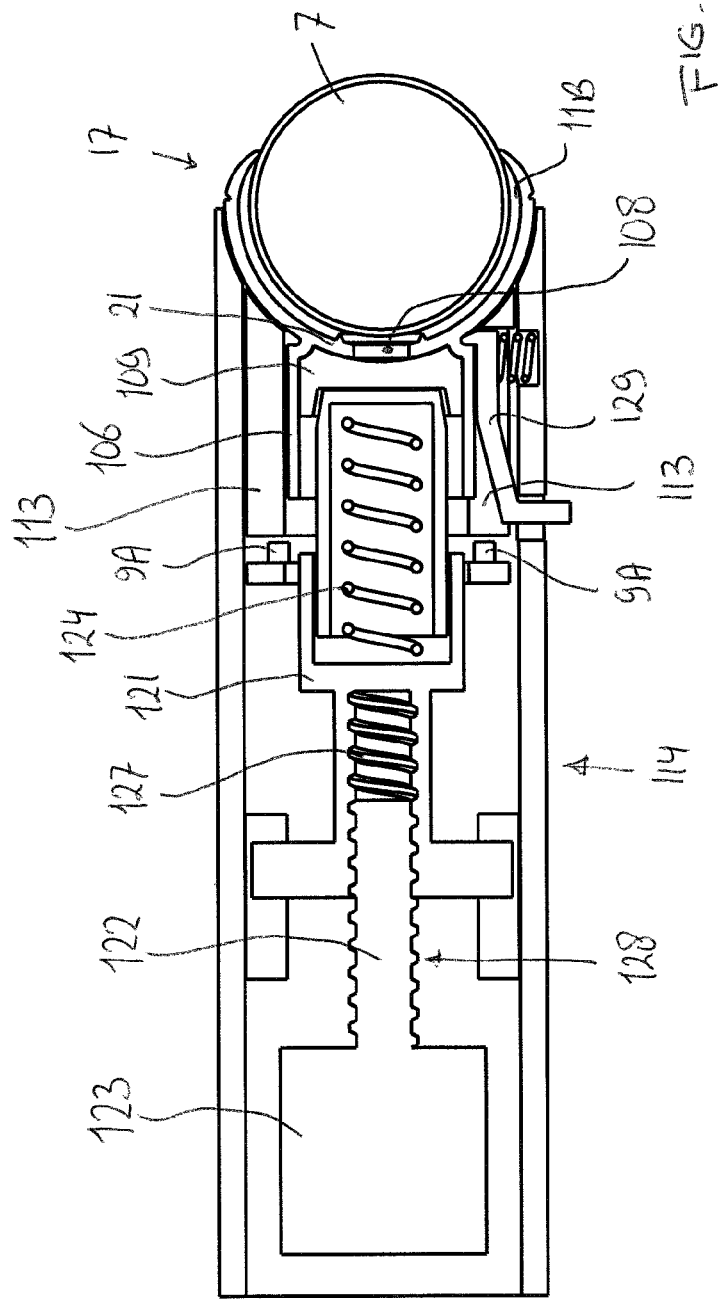

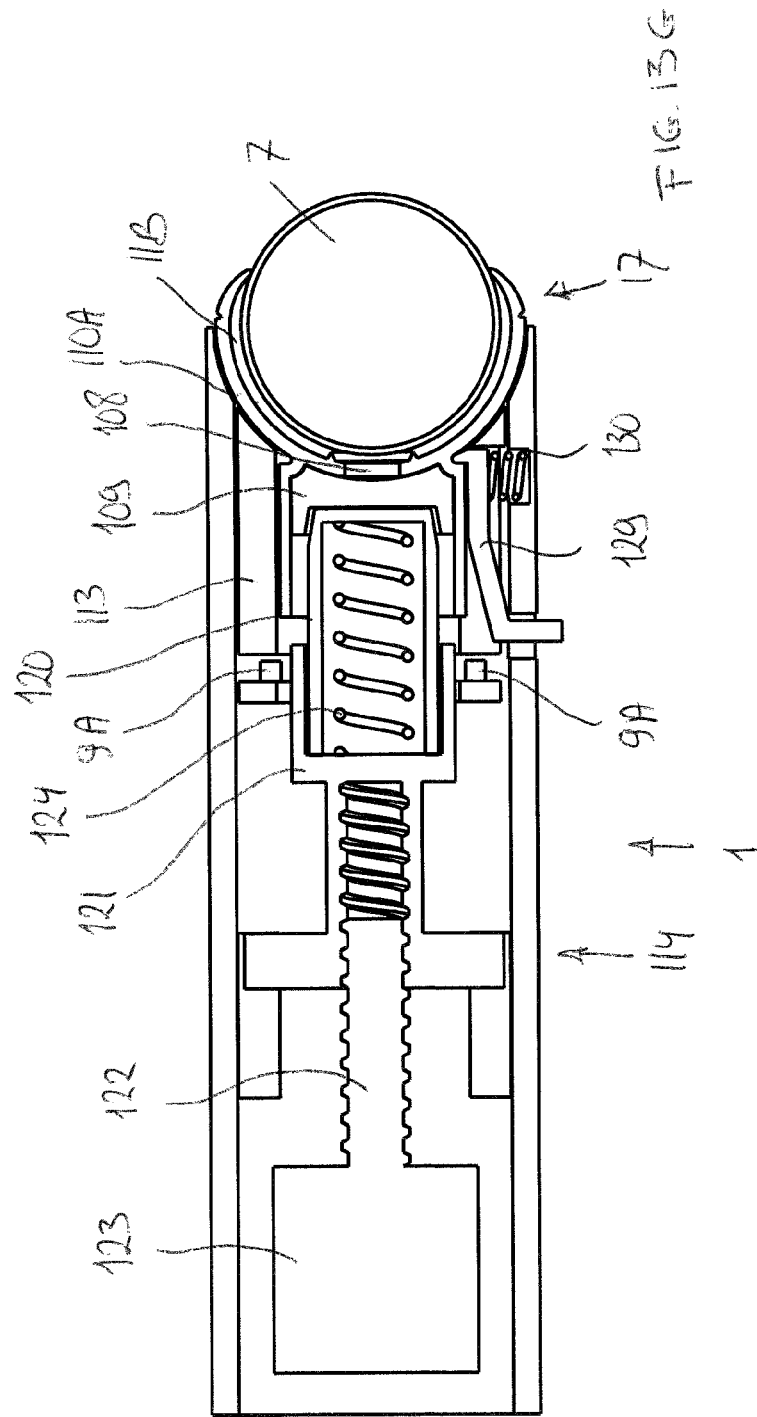

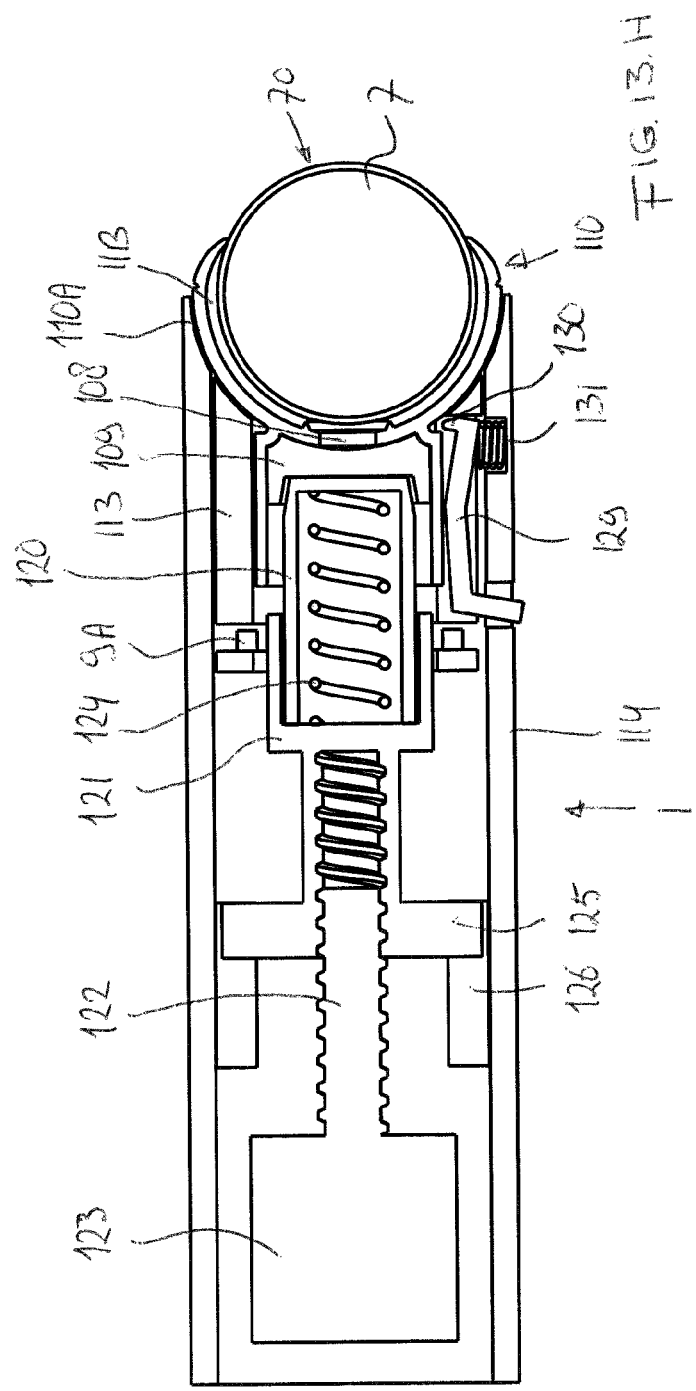

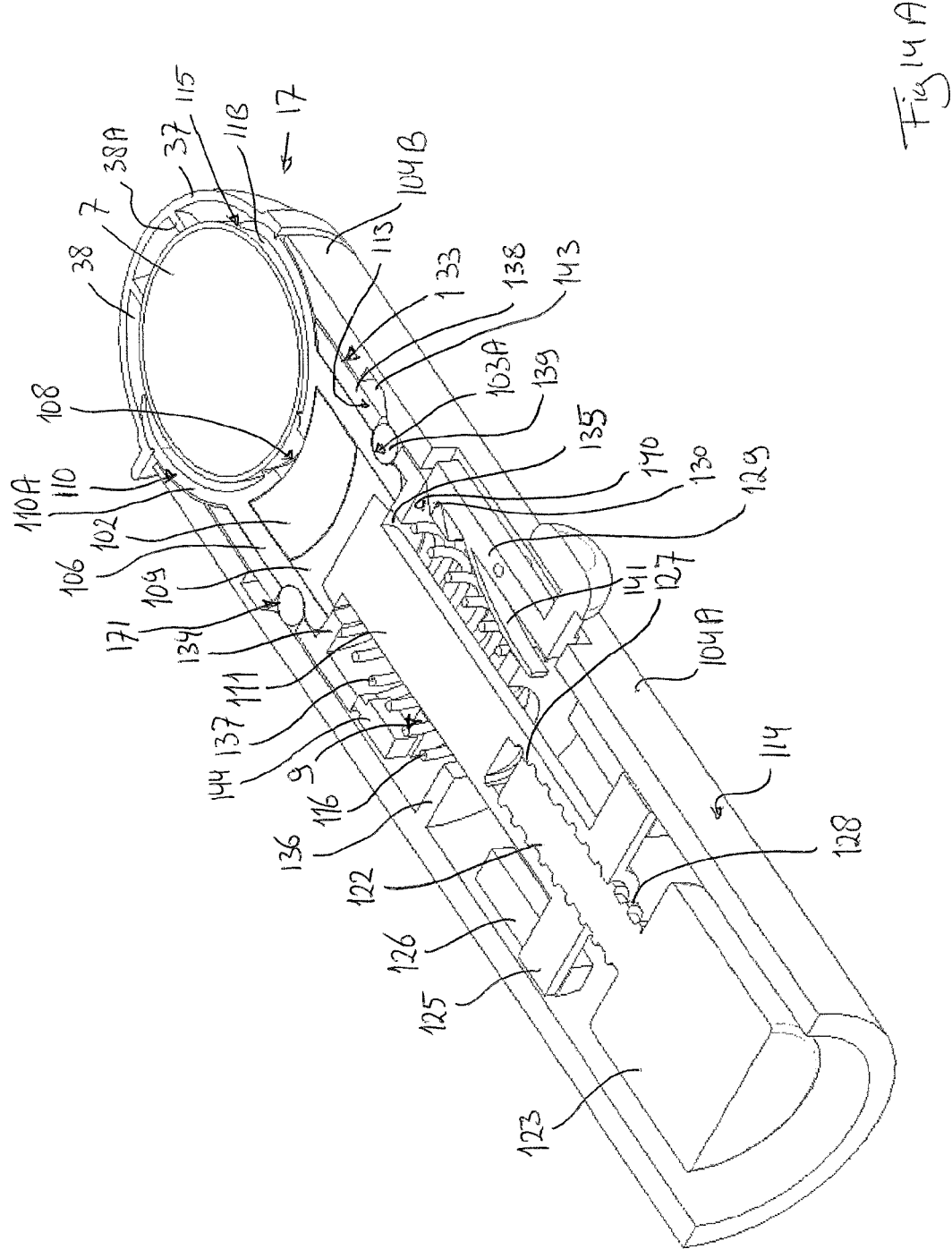

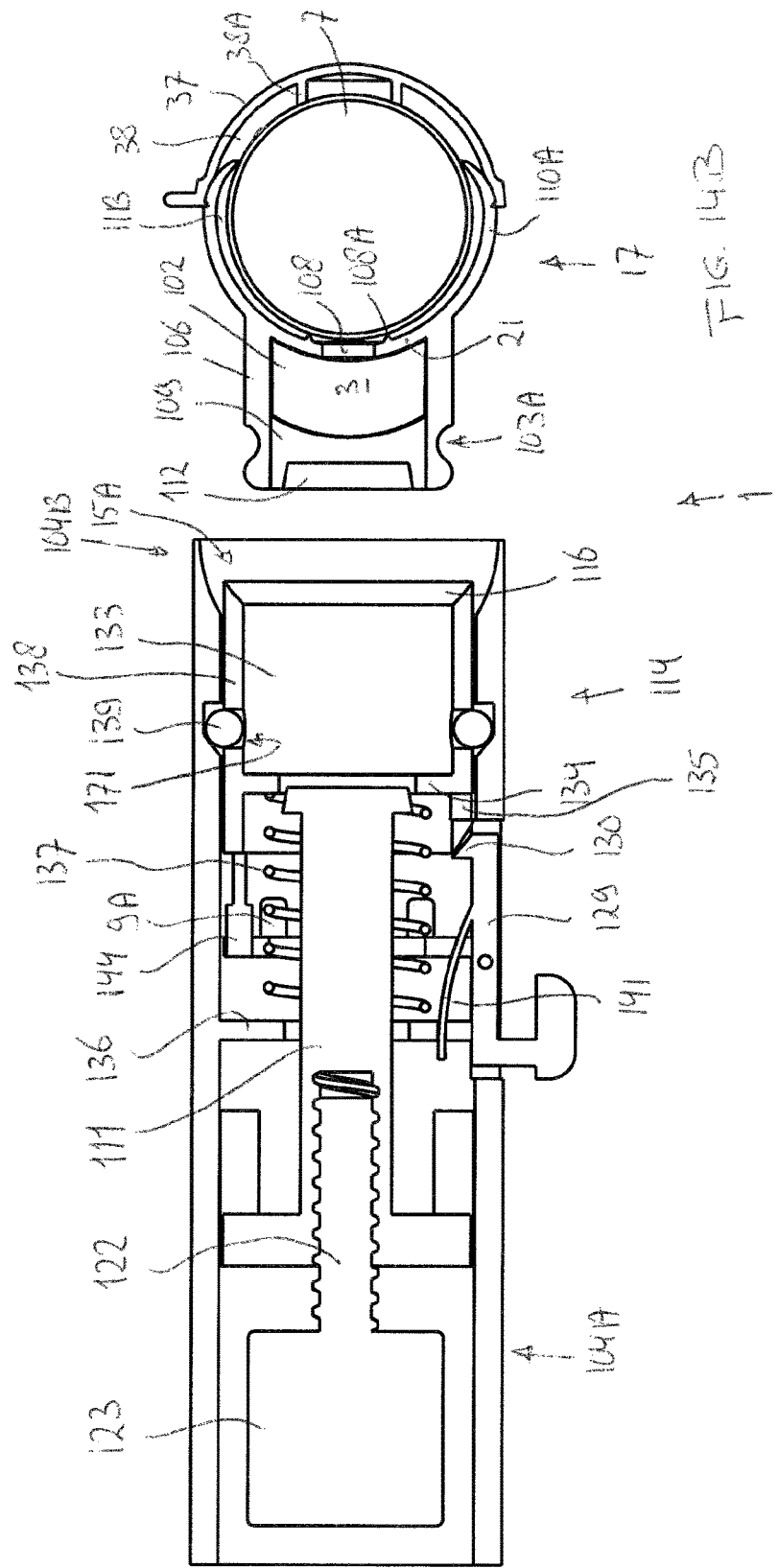

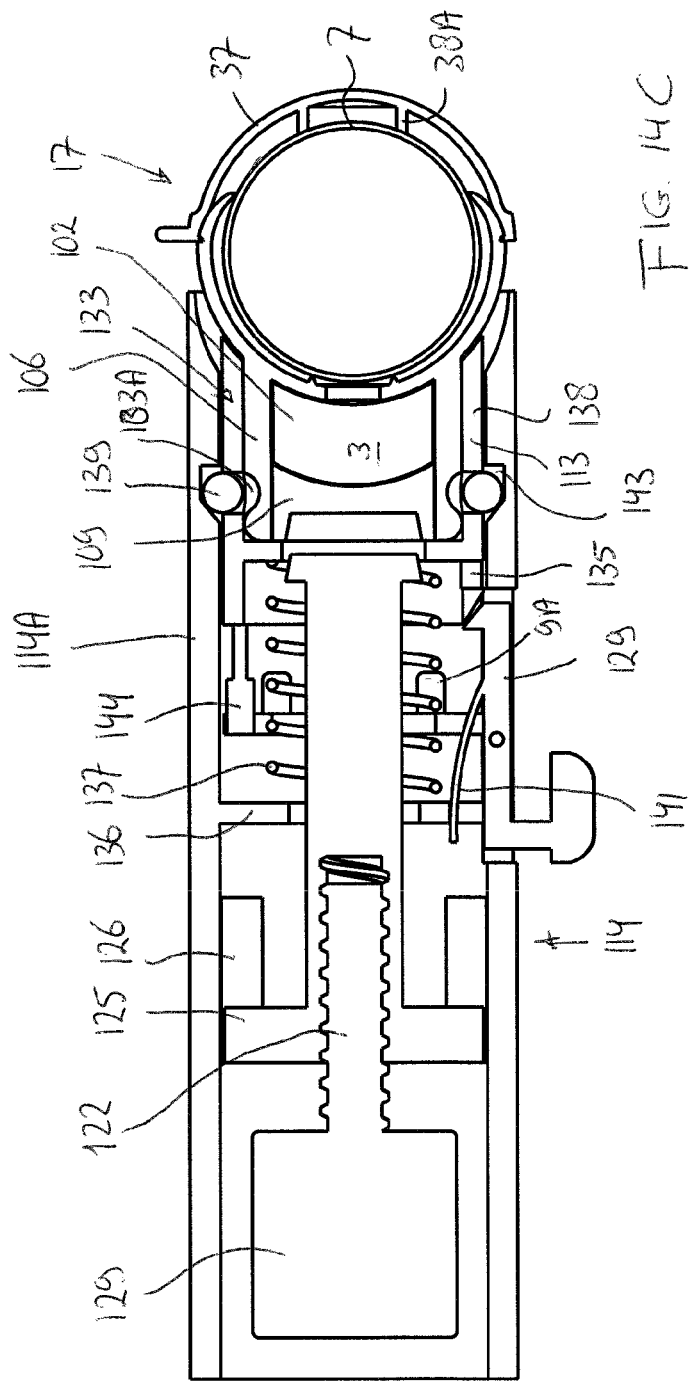

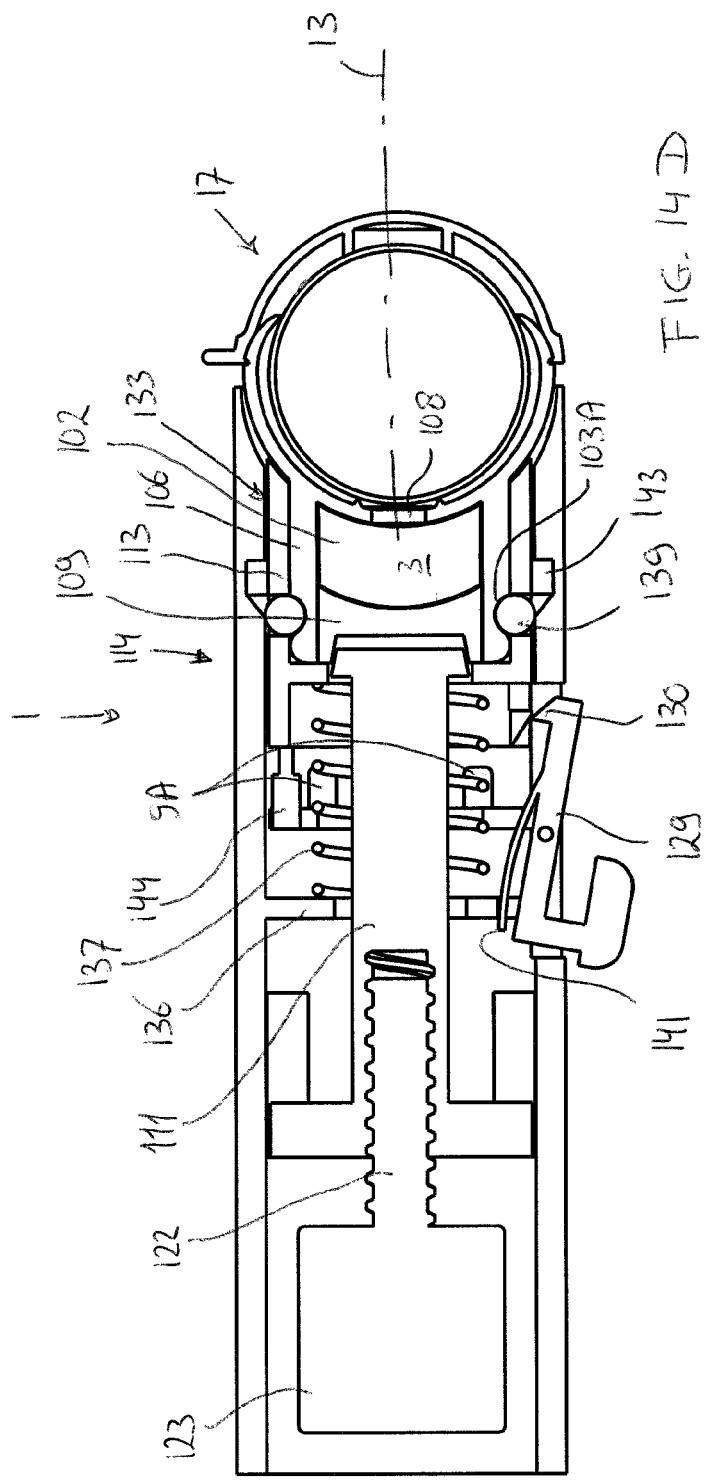

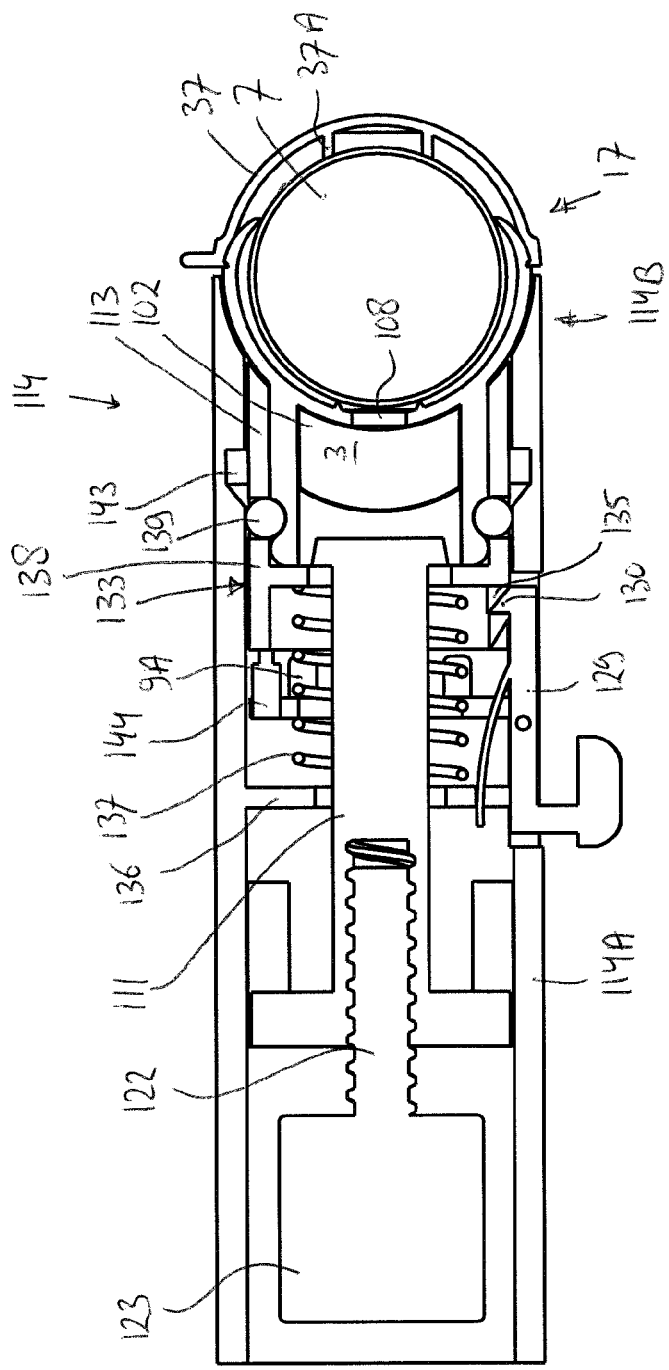

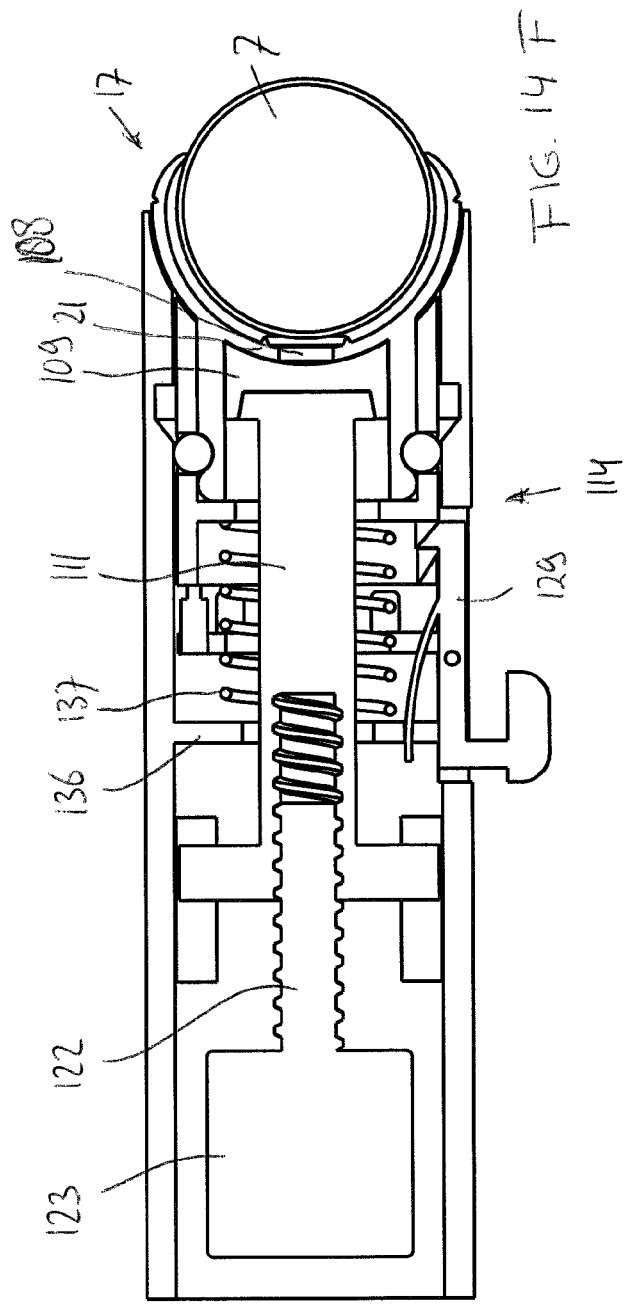

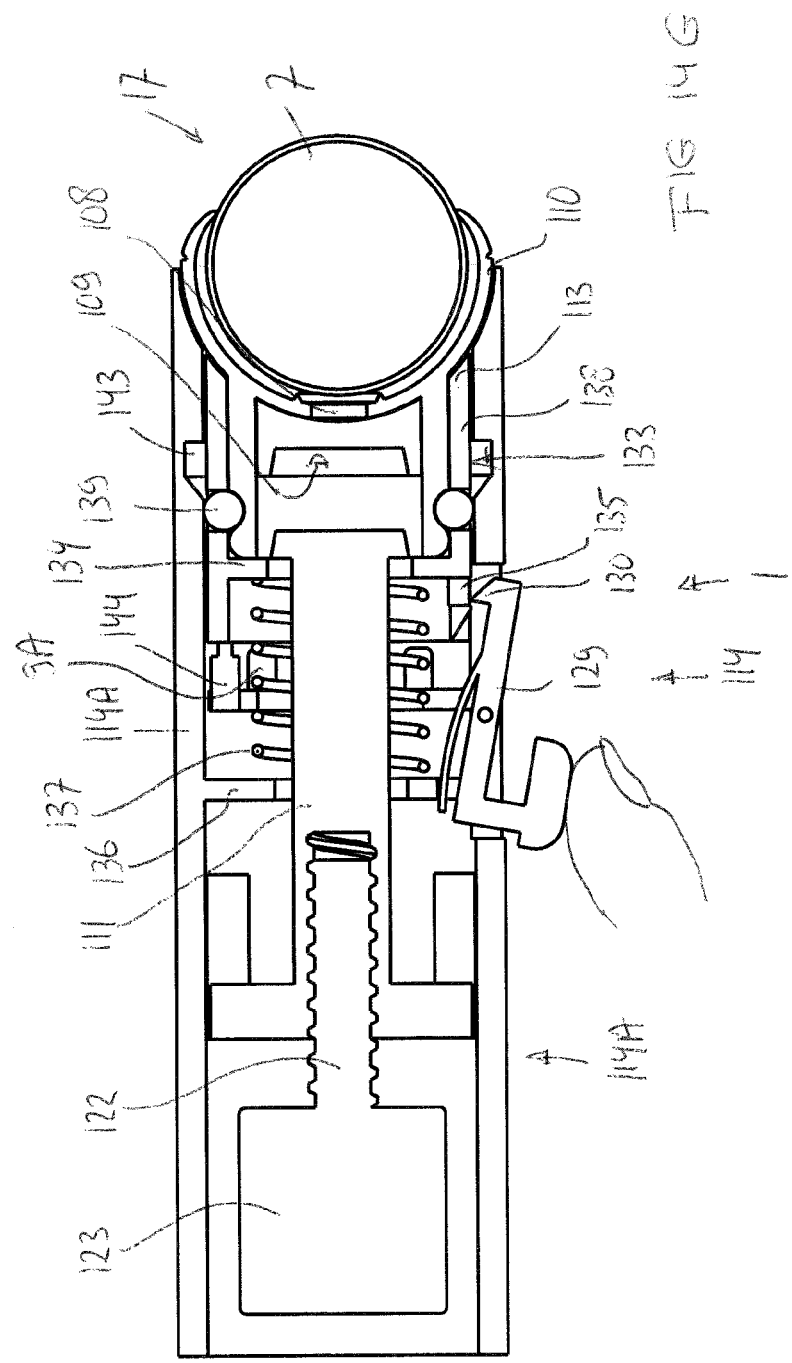

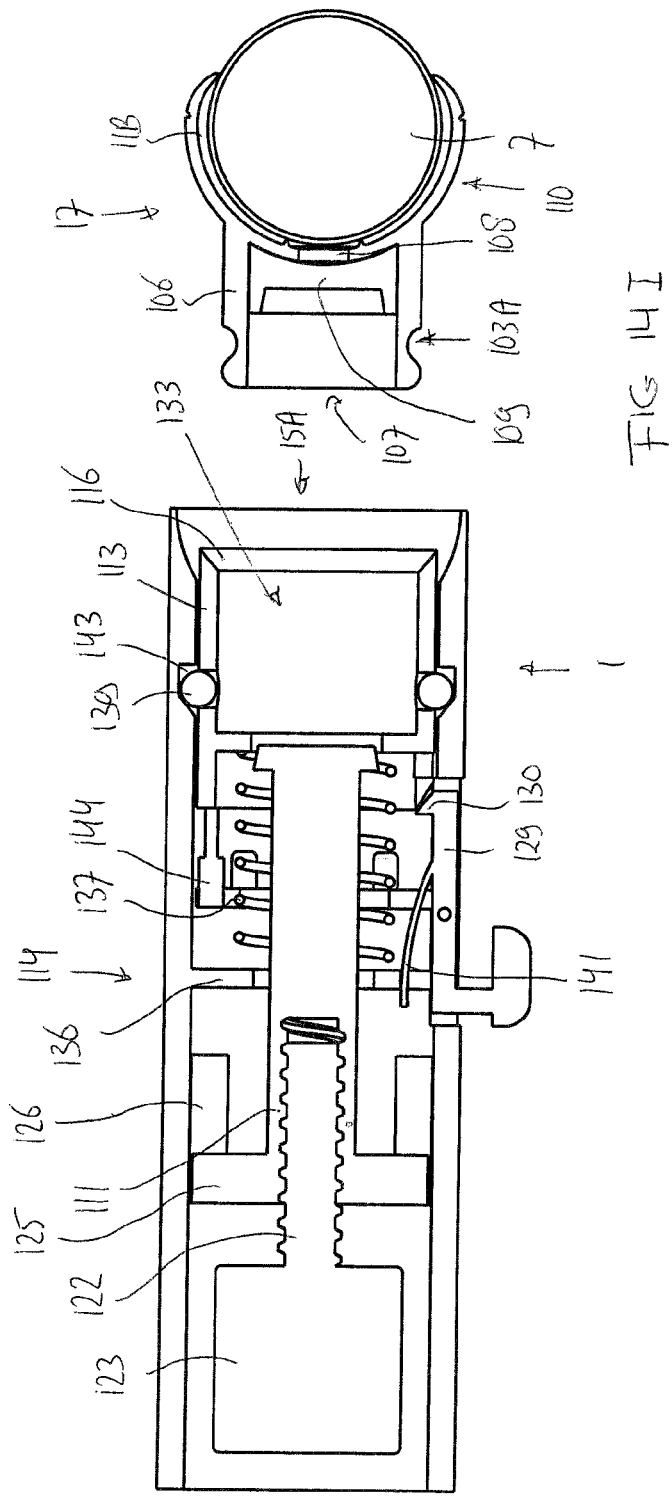

APPLICATOR AND CAPSULE FOR SUCH APPLICATOR

RELATED APPLICATION DATA

This application is a National Stage Application under 35 U.S.C. 371 of co-pending PCT application number PCT/EP2013/076776 designating the United States and filed Dec. 16, 2013; which claims the benefit of FR application number 1203445 and filed Dec. 17, 2012 and the benefit of FR application number 1203433 and filed Dec. 15, 2012 each of which are hereby incorporated by reference in their entireties.

The invention relates to an applicator for applying a product and light to an application surface, especially the dermis of a skin. The invention further relates to a capsule for applying at least a product to a surface, especially the epidermis of a skin.

The priority documents are comprised herein by reference.

For dispensing a product to a surface, such as a substance to a dermis of a skin, it is known to use dispensers with an applicator element such as a ball which can be rolled over said surface. The substance is taken up by the ball from a reservoir in the applicator and transferred to the surface over which the ball is rolled.

Moreover it is known to apply light to a surface, for example for optimizing effects of a substance applied to said surface.

From US2008/262394 an applicator is known for dispensing a light to human skin, which applicator is a hand piece comprising a rolling ball as a massaging element and a connector for connecting the hand piece to a light source in a control device. Light from said light source is passed to the hand piece though a light connection such as an optical fiber and then radiated through or alongside the ball onto the surface to be illuminated. The ball is held in the hand piece in a ball chamber. In one embodiment the hand piece is provided with a plurality of openings around the ball, or a gap around the ball, through which cooling/warming air/liquid or massage oil/lubricant may be delivered to the skin during treatment of the skin. In US2008/262394 such liquid to be dispensed is, during use, injected into the ball chamber through a tube connected to the hand piece, from a source outside the hand piece.

From DE3905517 a hand held device is known comprising a rolling ball in a ball chamber, surrounded by a reservoir containing a fluid to be dispensed. The fluid can be picked up by the ball when rolling and be dispensed onto the skin. Light can be radiated onto and through the ball for heating the ball and for light therapy.

An aim of the present disclosure is to provide an alternative system for dispensing a product and light onto a surface, such as onto the dermis of human skin. An aim of the present disclosure is to provide a capsule for dispensing a product onto a surface. An aim of the present disclosure is to provide an applicator system which can be hand held, comprising a light source and a reservoir for fluid to be dispensed through an applicator element such as a ball, with which small volumes of product can be dispensed, preferably in a well controlled manner. An aim of the present disclosure is to provide for a method and system for treating a surface, such as the dermis of skin, by applying a product and light onto said surface by an applicator element, with which a predetermined amount of product per period of time is dispensed onto said surface. An aim of the present disclosure is to provide an applicator system for applying a product and light onto a surface, such as human skin, in a hygienic and comfortable manner. Preferably such applicator can be used in any position.

At least one of these and/or other aims of the disclosure can be obtained with a system, applicator, capsule and/or method as disclosed in this disclosure.

In an aspect a capsule can be provided for distributing, on a surface of a living body, a product containing an active component or forming a cosmetic product, the capsule having a product distribution zone and comprising in a body, a supply of product which is in communication with the product distribution zone, and first linking means for removably securing the capsule to second linking means of a housing in which is disposed a light source.

In an aspect a product distribution device can be provided containing an active component for distribution on a surface of a living body and the radiation towards this surface, the device comprising a distribution capsule and a housing to which the capsule is secured in a removable manner, by first and second linking means, and in which is disposed the light source adapted for emitting said light ray(s) towards the product distribution zone.

In a further aspect a device can be provided for distributing, on a surface of a living body, a product containing an active component or forming a cosmetic product, and the release/discharge, at least as far as this surface, of energy in the form of (a) light wave(s), the device comprising a distribution zone of product on said surface and at least one light source emitting at least one light ray towards the surface.

In a still further aspect a capsule, can be provided, for example for use with a device as described here above, wherein the capsule comprises a ball rotatably mounted in a housing, wherein the housing comprises a reservoir having a movable and/or deformable wall, for containing product to be dispensed by the ball, and wherein the reservoir is in communication with a space between the ball and the housing through at least one opening. The opening is preferably relatively small. The reservoir preferably has a volume for a relatively small amount of product.

According to the present disclosure a capsule preferably is disposable and preferably comprises a relatively small amount of product to be dispensed, such as for example an amount sufficient for a single application cycle, which can for example comprises a series of dispense steps.

In a still further aspect a method can be provided for applying product and light to a surface, wherein a capsule comprising a reservoir containing product is releasably coupled to a housing comprising at least a light source and a control unit. The capsule comprises a movable element such as a ball onto which product from the reservoir can be fed for dispensing it to a surface by the ball, wherein light is transmitted from the light source through the capsule to the said surface prior to, during and/or after dispensing said product onto said surface, whereafter the capsule is removed from the housing and replaced by another capsule. The capsule comprises preferably a relatively small amount of product.

Other characteristics and advantages connected to the suggested solutions will become clear from the following detailed description of various embodiments where reference numerals refer to the annexed drawings provided by way of example and where:

FIG. 1 is an example of an applicator device of a product of which the interior is shown, according to a longitudinal central section, FIG. 2 is also a longitudinal central section, but only of the capsule containing the supply of product and the movable element.

FIG. 3 is a view according to FIG. 1, moreover partial and schematic, of the emission of the light radiation, FIGS. 4 and 5 shows safety means defining an interrupter which allows the emission of the light radiation to only intervene if it is axially supported and closes the electric circuit where the light source is situated; in FIG. 4 the circuit is open, in FIG. 5 the circuit is closed, FIG. 6 shows a joint action of the product/radiation on the skin, with a focal regulated on the level of the dermis, FIG. 7 is a central longitudinal section of a variant of the device FIG. 8 is a view of the only deep deformable piece 49 of FIG. 7, the arrows indicating the deformations.

FIG. 12 shows in perspective view schematically a device according to the present invention, in cross section along a mid-sectional plane comprising a longitudinal axis, for actively dispensing of product;

FIG. 12A shows in cross section schematically part of a applicator unit and a capsule, for a general discussion of active dispensing;

Figure 14H:
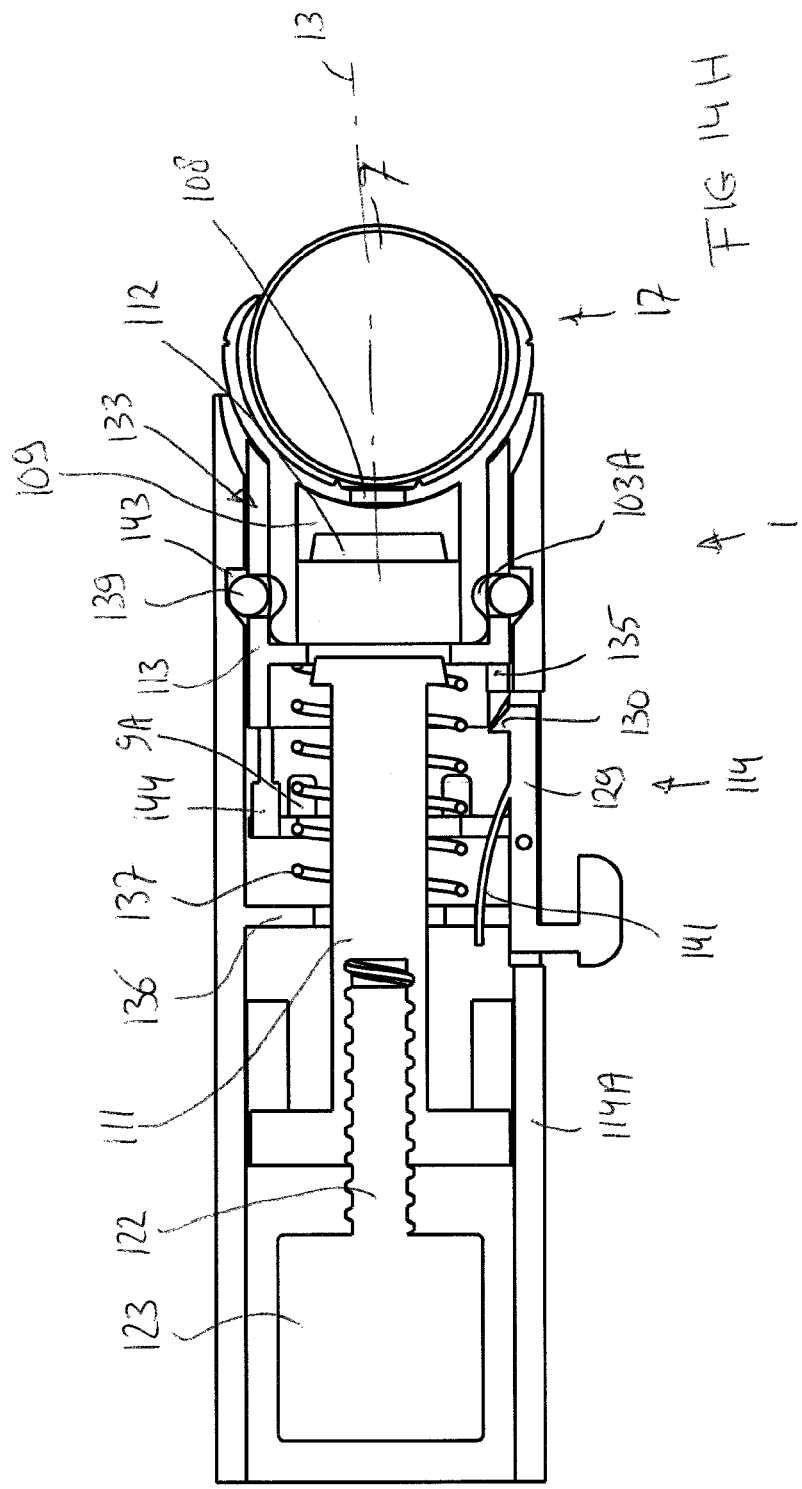
Figure 15A:
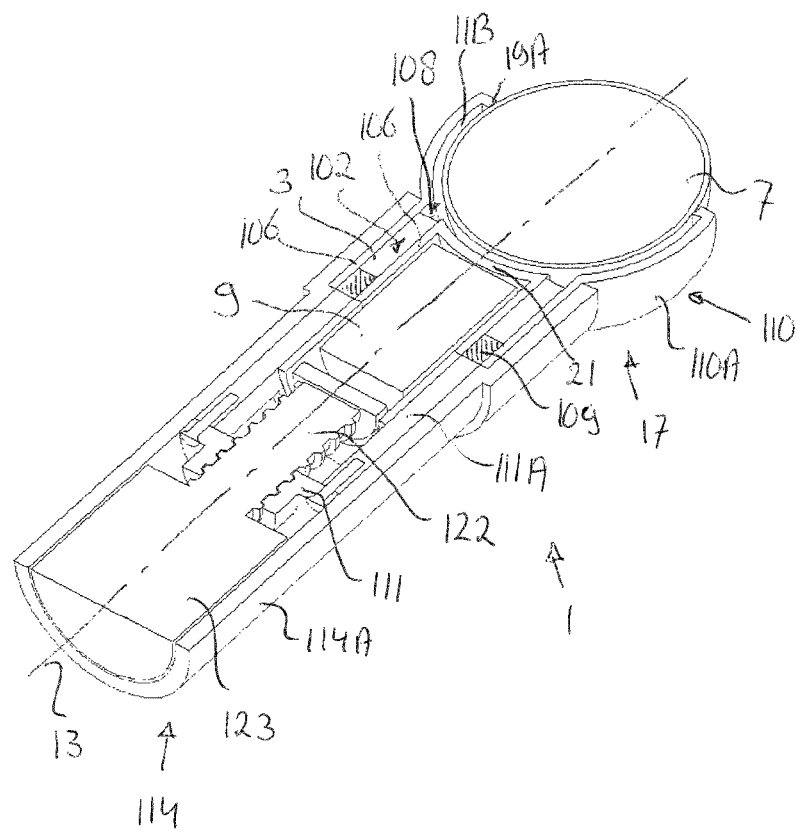
Figure 15B:
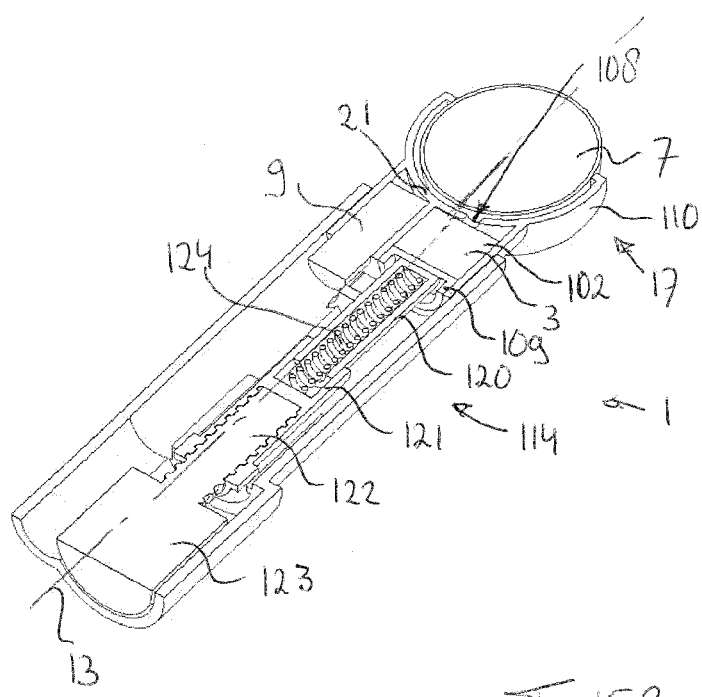
Figure 15C:
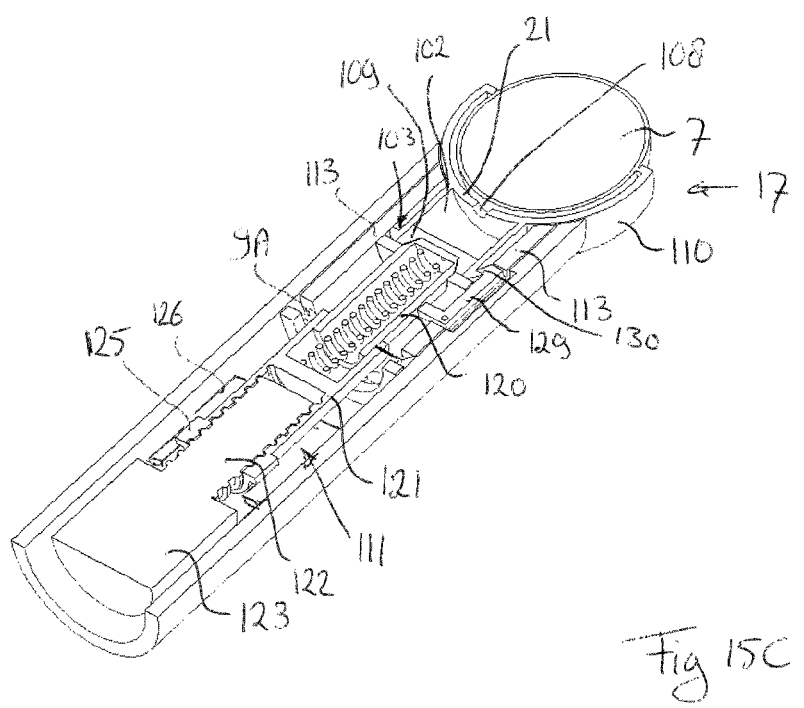

FIGS. 12B and C shows schematically a ball in an embodiment of a capsule housing, in cross sectional side view and frontal view;

FIG. 13A-I shows schematically a first embodiment of an assembly for active dispensing;

FIG. 14A-I shows schematically a second embodiment of an assembly for active dispensing;

FIG. 15A-C show three alternative embodiments of units 114 for active dispensing, as discussed with reference to especially FIG. 12-14, wherein the same or similar elements and features have the same or similar reference signs.

FIG. 15A shows an embodiment in which the capsule 17 comprises a ring shaped reservoir 102 with a ring shaded piston 109. The push rod 111 in this embodiment is again carried and movable by a motor 123 with spindle 122, and has a substantially cylindrical end portion 111A, adapted to engage the piston 109. Central near an insertion opening 15A of the unit 114 a light source 109 is provided, schematically shown as a rectangle, which can again contain one or more light elements such as but not limited to LED's, which can during use emit light through the wall 21 and the ball 7. In this embodiment one or more openings 108 can be provided for connecting the reservoir 102 with the space 11B around part of the ball 7.

FIG. 15B shows an embodiment in which the light source 9 and the reservoir 102 are positioned in side by side relationship when the capsule is coupled to the unit 114 and/or the housing 15. In this embodiment the drive mechanism comprising the motor 123 and push rod 111 has been shown substantially as shown in FIG. 13, with a spring 124 between a rod portion 121 and a front end portion 120. However, also other constructions can be considered, including but not limited to as shown in FIGS. 12 and 14. In this embodiment the opening 108 is shown sideways from a central axis 13, but if could also be positioned on the axis 13. Coupling between the capsule 17 and the unit 114 or housing 15 can be achieved in any suitable way, for example one as discussed here before. Due to the asymmetric form only one position can be chosen for insertion, contrary to the previous embodiments in which the cartridges could be rotational symmetrical, at least as far as the coupling is concerned.

FIG. 15C shows an embodiment of a unit 114 substantially similar to that of FIG. 13, in which however the arm 129 has been positioned and designed differently, such that the rod portion 121 can engage an end of the arm opposite the hook 130, such that when the piston 109 has been moved forward such that the reservoir 102 has been emptied, the rod portion 121 contacts the arm 129 and that upon a further movement of the rod portion 121 towards the capsule 17 the spring 124 is loaded, as described before, and the arm 1209 is pivoted by the rod portion 121, releasing the hook 130 from the groove 103. Thus the capsule 17 is automatically released from the unit 114 and device 1.

The present invention is by no means limited to the embodiments disclosed and discussed specifically in this description. Many alternative embodiments are considered to also have been disclosed or covered by the claims, including but not limited to combinations of embodiments or parts thereof as disclosed herein, including but not limited to embodiments and parts and features thereof as shown in and discussed with reference to the drawings.

In embodiments for example more than one reservoir could be provided, opening into the space around the movable element, such that components or products can be dispensed which will be mixed only upon application, for example components which would not provide a stable product over a longer period of time or which provide a chemical or physical reaction upon mixing which is desired to happen at or near said surface 5. The reservoir for active dispensing could be designed differently, for example as a flexible pouch, compressible by the push rod or by for example squeezing it. To this end for example the pouch could be pressurized by gas pressure or mechanically. Alternatively the reservoir could have a membrane or otherwise deformable wall in stead of the piston, which could be deformed by the push rod or in a different manner, for dispensing the product. A capsule could be provided with a light source, in stead of or additional to that in the holder 15. Multiple movable elements could be provided in a capsule, for example two or three such elements such as balls or rolls. A device according to the disclosure could be provided with an indicator system such as an alarm, for example by light, vibration and/or sound, indicating to a user that the applicator element should be moved to a next surface or part of a surface for dispensing a next amount of product in a next step. In embodiments the entire device could be disposable or reusable. However, disposable capsules 17 used with a reusable holder 15 are preferred.

These and other variations are considered to have been disclosed herein as well.

In this description embodiments of an applicator, capsule and method for dispensing are disclosed by way of examples only. In the different embodiments the same or similar parts and features have the same or similar reference signs. The products to be dispensed as discussed can be used in all embodiments, unless specifically discussed otherwise.

In this description wording like substantially or about should be understood as meaning that a value or property it refers to does not have to be met entirely. Small variations can be possible, such as for example 20% or less of the given value, for example less than 15%, such as for example 10% or less, or at least 5% or less.

In the present disclosure an applicator, also referred to as device 1 is to be understood as at least meaning a device comprising a housing which houses at least a light source and an energy source or connector for such energy source and a capsule releasably connected to or connectable to said housing, an applicator element and a reservoir for a product to be dispensed. Preferably the capsule comprises the applicator element and the reservoir.

In the present disclosure a capsule can be understood as meaning at least an element to be connected to or connectable to a housing as described, which capsule comprises at least first coupling or linking means or elements, for cooperation with second coupling or linking means or elements provided in and/or on the housing.

A capsule according to this description preferably is disposable, which can be understood at least as meaning that it contains a relatively small amount of product, especially an amount of product for a single treatment procedure, is made of relatively inexpensive materials and can be discarded after dispensing at least most of said small amount of product and/or after said single treatment procedure.

By using such disposable capsule, which could also be referred to as cartridge or pod, different advantages can be obtained. By using a new capsule for each treatment procedure it can be guaranteed that the right amount of product is dispensed during such procedure, or at least no more than a desired maximum. Moreover hygiene can be more easily guaranteed since the same capsule and especially the same applicator element will not be used for different treatments or by or for different users and/or surfaces. It may for example be prevented that contaminations picked up by the applicator element will be carried into a reservoir of product to be dispensed in more than one treatment procedure. Moreover the element that would normally require the best cleaning after use can now be discarded, limiting the necessity of meticulous cleaning. Furthermore it will be easy to switch between products to be dispensed. A further advantage can be that the quality of product contained inside the reservoir of said capsule can be guaranteed better, especially when the product may be susceptible to for example deterioration by aging or oxidation.

In this description a relatively small amount of product contained in the reservoir can for example be less than 10 ml, more specifically less than 5 ml, more in particular less than 3 ml, such as for example between 0.01 and 1.5 ml.

During use the product may be dispensed from the reservoir in a continuous or semi continuous flow, for example initiated by movement of the applicator element over the said surface. The supply of fluid to the applicator element can for example result from adhesion of the product to the moving applicator element, from gravity, from capillary effect or from a combination thereof.

In other embodiments during use the product may be actively fed to the applicator element, for example with a controlled flow and/or with a controlled, preferably predetermined amount per period of time. Actively fed can be understood as at least meaning that a positive force is applied to the product for feeding an amount of product to the applicator element. This can for example be achieved by a piston, or a movable or deformable wall of the reservoir, acting on the product under the influence of a displacement source or power source, such as but not limited to a motor or pump.

Preferably the light source is provided in the housing. In embodiments the light source can comprise or be formed by one or more LED's. The light source can have different elements for different light frequencies. One or more light guides can be provided for guiding the light through part of the housing, from the light source to the capsule when mounted properly. A light guide can for example comprise one or more optical fibers or a light transmitting element or elements, such as an element, for example made of a transparent plastic such as but not limited to PMMA, Perspex, PC or the like, or of glass. The capsule can be provided with one or more windows or openings or be made of a light transmitting material, for allowing light from the light source cq light guide to pass into the capsule and/or into and/or through the applicator element and/or passed the applicator element.

The disclosure inter alia relates to a capsule (which can serve as applicator device) and a device which provides energy in the form of light radiation waves. The device enables at the same time the application of a product containing an active component or forming a cosmetic product, and light radiation of a wave length selected on or just below an application surface, in particular the dermis of a skin.

More in general, objectives of the present invention can be
a) as desired, capsules of various geometries which allow the application of several different products or with an optimized preservation capacity, or further still with an optimized quantity, and
b) a combined device allowing:
at the same time, the distribution (or spread, and preferably application, hence putting on) of a product, containing an active component or forming a cosmetic product, on a surface of a living body,
and the discharge of energy in the form of (a) light wave(s), via for instance electroluminescent diodes (LED's) passing from UV to infrared, thus creating an interaction between product and energy, on or below the said surface.

Also envisaged is:
a capsule with which the field of application of the device can be enlarged, in particular for treatment of the skin,
and a device which improves a synergic reaction in or on the epidermis, between radiation and an activation of the product.

It is understood that here, 'product' is understood to mean a substance, containing an active component or forming a cosmetic product. What is concerned here is a product for local (topical) application, which is either a cosmetic product, or a medicine, with its (their) active component(s). It has a more or less fluid consistency and composition, with a possibly variable viscosity and texture according to the sought after benefits. A serum can be involved, or a liquid emulsion, without excluding slightly thicker consistencies, if necessary. Preferably, the active component has a bio-inductive effect.

Advantageously, the product contained in the capsule can be such that it reacts to a given wavelength and a given time of exposure to radiation.

An object of the present invention is a solution with which the substance to be applied is optimally protected, to select the substance depending on the application to be considered, while always benefitting, on the entire device, from the light radiation which is favorable to the efficiency of the product, once it is applied.

In addition to the skin, the distribution surface for the product can be the external surface of a living organ, in particular an organ that needs to heal.

The proposed capsule can be such that it provides a product distribution zone, and comprises: in a body, a supply of product which is in communication with the distribution zone of the product, and first linking means, and second linking means, for removably connecting, between the capsule and a housing in which is disposed a light source. The first and second linking means can be situated at a distance from the light ray(s) coming from the light source.

The exchangeability of the capsule, and therefore the changing of product is thus improved.

Another advantage is, if desired, that a capsule is provided which can be used once (mono-dose), and is especially hygienic as thus, the risks of proliferation of bacteria and oxidation of the product (and of the active component in particular) are restricted. Furthermore, the same housing can receive various capsules, especially having different forms and/or content.

To simplify the way of activating the product or the bodily environment where it is placed, it is recommended that preferably, the emitted ray(s) pass through the product distribution zone mentioned.

For a given product, it is possible to reduce the exposure to radiation (filtering of the rays on the capsule) by regulating the focal point while changing the optical indexes of the transparent parts of the capsule, modifying the diameter of the ellipsoid of revolution that can serve as applicator element (see element 7 hereinafter), which diameter can be adjusted depending on the viscosity of the product and/or modifying the supply of product under the ellipsoid of revolution (in particular ball), again depending on for example the viscosity.

It is further recommended that the device comprises product applicator means, for applying the product application (putting it on) on said surface, and means for starting the emission of the ray by the light source, while these starting means are activatable by the user at a distance from the distribution zone and/or with the intermediary of applicator means for allowing the start of the emission while the product is applied via said distribution zone, favorably such that then, the ray passes through the applied product.

Furthermore, the safety of the user with regard to the emitted light can be checked.

In order to improve a uniform distribution of the product and its penetration into the thickness of the dermis or the surface of the organ, which is a priori porous, it is recommended that the capsule comprises a movable element having an outer wall, preferably convex, which contributes to or ensures the product application, and/or which is movable on said surface by the intermediary of the distribution zone of the product.

This is advantageous to the compactness of the device and to an interaction between the application of the product and a possible "massaging" effect favorable to the penetration thereof into the surface, which is porous.

In order to improve the interaction between the delivered light energy and the applied product, it is advised that the light source emits the ray(s) towards the surface, through the distribution zone.

In order to ensure a high-end distribution and to improve a uniformity of this distribution, it is further advised that the device comprises a product supply which is in communication with the product distribution zone which supply is preferably enclosed in a protective manner.

To reduce oxidation of the product contained in the device, it is recommended that prior to the first distribution, a protective foil or cap is provided over the movable element.

Furthermore a protective, mobile or removable hood prevents radiation towards the eyes of the user at the time of recharging, and which can form a protection against oxidation.

In order to optimize the application of the product as well as the passage of the ray as far as the surface mentioned, it is recommended that the device provides an axis along which the ray is emitted towards the surface, while the product supply is situated either at least essentially transversely to the axis mentioned or around this axis. In the first case, the ray does not pass through the product, and in the second case, it does. This should be taken into account in determining the focal point.

To further improve the application of the product without disturbing the passage of the emitted light ray(s), it is advised that the movable element provides the product distribution zone. Thus, the synergy product/light can be improved.

Still with respect to a favorable distribution of the product and this synergy, it is recommended that the movable element pivots about at least one pivotal axis and has a convex exterior wall, and/or that the movable element has an ovoid form, preferably an ellipsoid of revolution, and pivots on the body, and/or rotates in the body.

For protection of the product, without this interfering with the removable connection between the capsule and the body of the device bearing the light source, or with the favorable emission of the ray(s), the capsule can have a cavity which is open towards the exterior to one side and have a blind flange, preferably transparent to rays, said first linking means of the capsule being situated towards this blind flange, and lateral relative thereto.

Thus, at the same time, it is ensured and simplified both the separation and the axial connection between the housing bearer of the light source and the capsule, without hindering the free passage of the light rays/radiation.

With respect to the device itself, it is understood that it is provided with the precited distribution capsule, and the housing to which this capsule is therefore secured in a removable manner, by first and second linking means, and in which is disposed the light source adapted to emit, toward the product distribution zone, and therefore the distribution surface, the light ray(s) or at least one wavelength.

For reasons already given, it is recommended that the light source emits ray(s) through the product application means, and preferably, that the product applicator means comprise, as movable element, an ovoid form through which the ray(s) can pass. Thus the above-mentioned synergy is improved and with this ovoid form, preferably an ellipsoid of revolution, an optical system can be created. The ovoid form in its housing can be arranged to adapt to the viscosity of the substance.

In a favorable embodiment, for a simple and efficient optical system, the optical index of the movable element is constant over the entire mobile element, which is uniformly solid or hollow.

In order to control the focal depth, and the point of convergence of the energy, the product distribution zone, and therefore preferably the movable element, can be designed from different materials, solid, hollow or liquid. Thus, the focal point can be regulated to a certain depth in the surface, in particular the epidermis, so as to optimize the effect of the chosen product. With the same purpose, the dimensioning of the ovoid form and in particular its diameter and the distance relative to the source enable regulation of a focal distance and concentration of the light flow to a certain distance below the application surface concerned, in particular the dermis.

Again for the performance of the synergy between the application of the product and the effect provided by the radiation, it is recommended to limit the oxidation of the product while considering the device as a whole of two parts comprising a housing in which the light source is accommodated and a capsule, movably secured to the housing and containing the supply of product and the product distribution zone. Thus, the capsule can be a recharge/refill which allows the use of a disposable one-time-dose of product. The amount of product can then be a one day dose of treatment.

The dose of product contained in the capsule can be especially protected against oxidation by the packaging formed by the capsule, while removal of a sealed protective film or cap only takes a few seconds just before the application of the product.

Alternatively, or preferably additionally, a lid is provided in a removable manner, for isolating the supply of product from the environment, whereby a volume is covered at an atmosphere intended to protect the product from oxidation prior to the first opening of the lid.

For the transmission of the ray towards the surface and the protection, it is advised that a first wall transparent to the ray is provided, interposed between the light source and the product distribution zone, and which allows the ray to pass through this zone.

It is furthermore recommended that this wall has a dimension that is sufficiently great for allowing the ray to concentrate on the zone of the exterior, convex wall of the movable element that comes into contact with the surface of the body, or beyond.

In this respect, it is favorable for the efficiency of the synergy between the applied product and the ray emitted towards the application surface, that the passage of the ray in the optical system formed in the device concentrates this ray in the contact zone, there where the product distribution zone comes into contact with the surface to be treated, or slightly beyond, more deeply into this surface.

In this respect, a well chosen solution is a priori a solution where the movable element having the distribution zone and/or the supply which feeds it with product, define an optical device as such, while the application means are in contact with the surface of the body, the passage of the optical rays in the device concentrate these rays in the contact zone, this movable element is integrally formed to concentrate the ray(s) on or a few millimeters beyond the distribution zone mentioned, which is a contact zone with the surface of the body in a manner such that, with the distribution surface being the skin, the focal point can be located in the dermis or, at most, between the dermis and the epidermis.

If the solution with the refill capsule is considered, it is further recommended that the first wall transparent to the ray be airtightly secured to for example an integral part of the capsule with respect to the product. This especially increases the protection from oxidation.

The same holds for the embodiment where, as is recommended here, in the housing, the light source is protected by a second wall transparent to the ray which, with the capsule and housing assembled, is situated opposite to the first transparent wall. In principle, only air separates the opposing first and second walls.

To promote the use of the device on numerous locations of the surface in question, as well as the spread of the product on the movable element, it is further recommended that this movable element be ellipsoid of revolution, in particular a sphere or a more oval form, pivoting in all directions, in or on the device.

For the use and the ergonomics of the solution proposed to the user, it is advised that the housing of the device provides a push-handle for moving the movable element, this push-handle extending in a direction towards the movable element and batteries or a feed battery for the light source which are arranged in the push-handle.

For safe use, and taking into account the light intensity of the ray which might damage the retina of a user when catching the ray, it is provided, while ensuring a simple functioning of the device and avoiding unnecessary loss of electric energy, that on the device, starting means for the emission of the light by the light source are provided which can comprise a first body, mounted with the application means and itself translatably mounted along an axis relative to a second body of the device, between a first position where the first and second body are axially distanced one from the other while opening (interrupting) an electric circuit comprising the light source which, in this manner, cannot emit a ray, and a second position where, by pushing the movable element along this axis, the first and second body are axially brought closer to each other while closing the electric circuit so that the light source emits its ray, and biasing means, provided between the first and second body for returning them in a natural manner to the first position. Thus, pressure on the movable element starts the electric contact, and switches on the device. Light will be emitted only in the event of a pushing motion on the movable element. In rest, no light whatsoever will be emitted. This, preferably together with the presence of an opaque protective lid movably mounted on the movable part forming the applicator of the product, allows for combining proper protection of the product in supply (via the lid) and safety of use, wherein there will be emission of light only if, with removed cap, the movable element is pressed in. If not, the starting means comprise an interrupter on/off and preferably the above mentioned protective cover.

With respect to the manner of distribution of the product on the surface involved and the emission of radiation, it is advised for reasons already given hereinabove, that the method comprises application of the product on the product distribution zone of the device mentioned, and the emission of radiation towards this distribution zone, preferably together with the application of the product.

To improve the synergy between the distribution and the emission of radiation, while simplifying the use, it is recommended that the product be provided in a product supply of the device, that the product is distributed by rolling a movable element of the device, in contact with the product in the product supply, and that, by a light source of the device, a surface of an exterior wall of the movable element be lighted, through the movable element.

However, for certain products and certain applications, it is provided that the product can easily be placed in the luminous path, whereby the focal point is modified and the reaction of the cells is improved.

The bottom of the capsule is designed in a material transparent to the radiation, or can be optically filtering, which allows for the selection, on a given capsule, of wave lengths adapted to the conditions of use. It is advised for a specific product, for an identical wavelength emission of the light source device to provide the light source emitting rays in a housing of the device, —to provide the product in a product supply of a capsule comprising product application means, and also associated to the device, whereby the capsule forms an optical system, to movably secure the capsule to the housing and to modify the refraction index(es) of the optical system of the capsule traversed by the ray, depending on the product, for example for and/or changing the emitted light frequency changing the focal point.

For reasons of ergonomics and ease of handling of the device, it is recommended that, with the capsule secured to the housing, the housing has a push handle for moving the movable element, while advantageously extending in a direction towards this movable element and the light source, and wherein the feed batteries of the light source are arranged.

To check the interaction between the produced light energy and the distributed product, and/or the safety of the user with respect to the emitted light, it is recommended that starting means are provided, activatable by the user at a distance from the distribution zone and/or by the intermediary of the movable element, thus allowing for the start of the emission of the ray by the light source when the product is distributed via the distribution zone mentioned, so that the light flow passes through the distributed product.

With respect to distributing the product over the surface concerned, and creating warmth and/or photonic activation of the constituent cells of this living surface, by light radiation thereon, it is provided to distribute the product on this surface, via the product application means, and, preferably simultaneously, to emit towards this surface the radiation coming form the light source, while adapting the focal point thus that photo-biomodulation is effected, which preferably penetrates as far as the fibroblasts responsible for the production of collagen and blood vessels.

To reach the surface to be treated, the radiation coming from the light source can pass through the application means and in particular the movable element. However, another configuration can be envisaged: have the ray(s) pass alongside the applicator element, in particular around, via for instance a series of electroluminescent diodes disposed in a circle.

Figure 1:
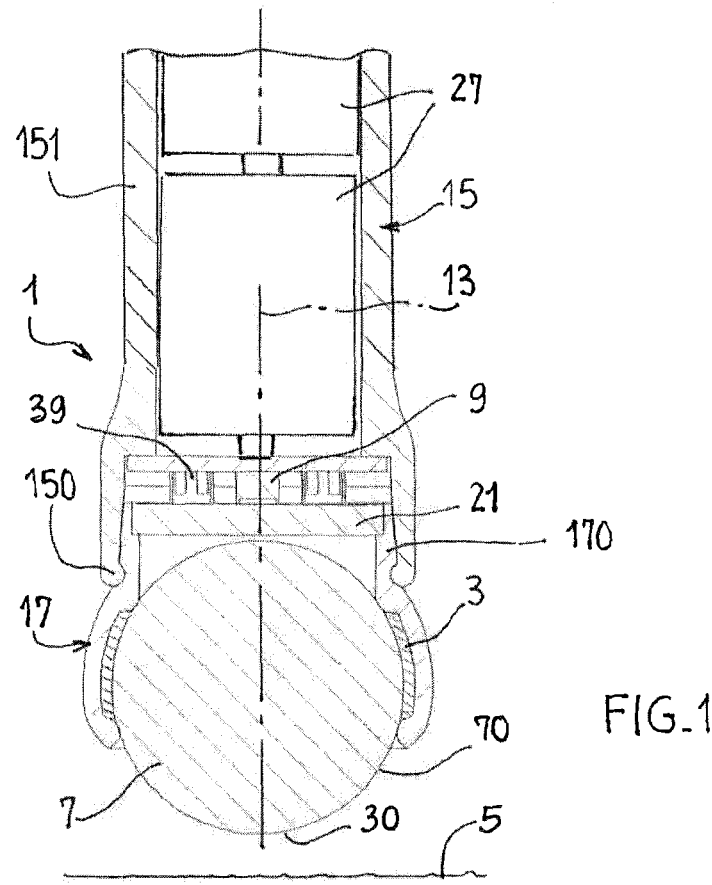

FIG. 1 shows a distribution device 1 of a product 3 of the mentioned type, on a surface 5 of a living body and the discharge to the surface 5 of energy in the form of light ray(s) or illumination of this surface.

The product 3 contains an active component or forms a cosmetic product.

It is preferred that it has the consistency of a liquid or a creme.

The surface 5 can be skin surface, or (epi)dermis. Also, the surface of an organ of the human body can be involved, including in internal organ accessible through operation, and which can be healed. More in general are involved cutaneous applications, treatment of acne, stretch marks, cicatrization, such as but not limited to skin or internal organs.

The device 1 has a zone 30 of distribution of this product to the surface 5, there where product is present and where it can be in contact with the surface to be covered.

For distributing the product and optimally activating it, the device 1 can comprise:
an applicator means 7 having a rounded exterior wall 70, and a light source 9 consisting of or comprising an emitter of one or several rays 90 towards the surface 5, preferably through the element 7, having a convex exterior wall 70.

Advantageously, the applicator element is movable in and/or on the body of the device.

Advantageously, the source 9 comprises one or several electroluminescent diodes. They can emit light according to different wavelengths, thus allowing an adaptation of the effect on, or in, the surface 5, preferably depending on the product 3.

Here, the product 3 is liquid and rather fluid. Preferably, it has a viscosity that allows the product to be spread substantially uniformly over the distribution zone, during the exposition time to (a) selected illumination/(light) wave length(s).

The movable element is preferably ellipsoid of revolution ovoid, in particular a ball, whereas preferably the ray(s) can pass through it.

Here, a solid, transparent glass ball or solid polymer ball, or containing another product, solid or liquid can be involved. Alternatively the ball can be a hollow ball, for example a plastic ball.

In a preferred embodiment, the ball allows the passage of wavelengths between 400 and 1400 nm. Its diameter can for example be between 8-12 mm, although it can be smaller or larger.

A filter color can be added to the device, for instance to the movable element such as the ball, for selectively avoiding the transmission of certain wavelengths to the surface, this to augment the efficiency of a specific product, or for protecting it.

This movable element is pivotally mounted about at least one pivotal axis and it can be seen in the drawings that it is preferred that the exterior wall 70 has a convex exterior.

Although for instance a cylindrical or ovoid shape is possible, with, in that case, a movable element 7 mounted a priori pivotally around a single rotational axis perpendicular to the direction 13, it is recommended that the movable element 7 be ovoid, preferably an ellipsoid of revolution, has an ovoid shape such as a ball pivoting freely in all directions, in or on the device.

This improves a substantially uniform spread of product 3 and of the light on the surface 5, whatever the orientation in space of the device may be relative to the surface 5. Advantageously, the ellipsoid of revolution or ovoid shape, especially ball shaped, has a diameter which allows it to pass over all the parts of the face.

The device 1 also comprises a supply 11 of product which is in communication with the distribution zone 30, here the movable element 7.

In this respect, it is recommended that the product distribution zone 30 is situated on the movable element 7, here, in the Figures, at the surface of the exterior convex (rounded) wall 70.

To avoid ray/product interference to a high degree, it is recommended that the supply of product 11 is situated transversely relative to the axis 13 parallel to the direction the ray 90 is initially emitted in, towards the surface 5. But this is not necessary: provision in a rear zone, behind the applicator means 7 is also possible (see zone 11a in FIG. 2, or 11 in FIG. 7 and following). In FIG. 12-15 further possible positions and solutions for the supply of product are discussed. In this respect it should be noted that supply of product may be understood as being formed by or comprising a reservoir 102 for product 3.

Figure 6:
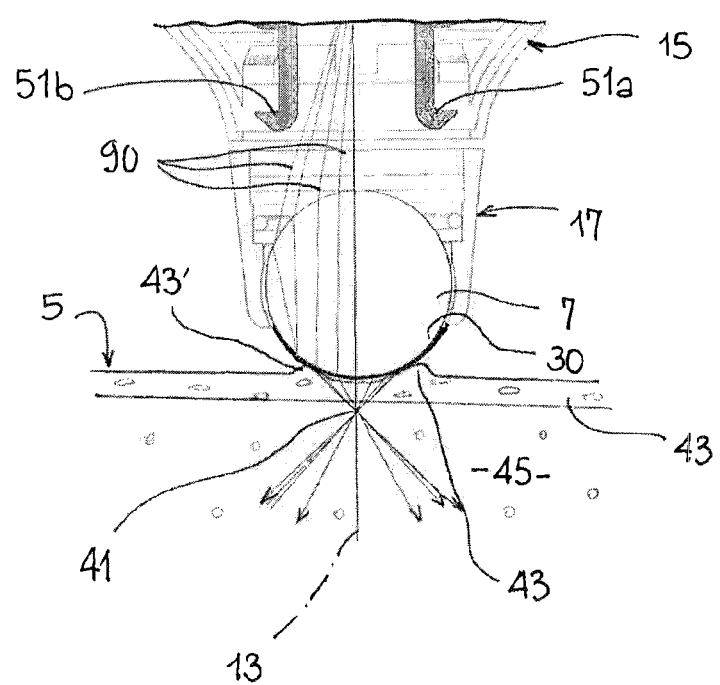

To further improve the synergy between product and emitted ray(s), it is recommended that the passage of the light or optic ray 90 in the device concentrates this light in the zone 25 where the exterior, convex wall 70 of the movable element 7 comes into contact with the surface 5, or some millimeters beyond, as shown in FIG. 6. Alternatively the design may be such that the light is spread over a wider surface area, for example by refraction by the ball 7 and/or by other parts in or of the housing 15 and/or capsule 17, as indicated in e.g. FIG. 3.

With respect to FIG. 6, the point 41 where the energy is the greatest is the location of the optical focus defined by the refraction indexes of the whole of the optical system. This focal point can be modified on the exchangeable capsule 17 (see further), for increasing the efficiency of a product, through changing the refraction indexes of the optical path, i.e. by modifying the materials, or by designing parts in different materials.

Still with respect to FIG. 6, it is clear that the distribution zone 30 of this product, here the exterior surface of the movable applicator 7 applied on the epidermis 43 of the skin of a patient, has a massaging effect on this epidermis, shown as for example small bumps 43', and improves the depth penetration towards the dermis 45 of the product that covers this surface.

Especially when the focal point 41 is in the dermis, the emitted light can be infrared light.

On the device, optionally, flexible ring-shaped lips 19a, 19b can ensure the airtightness before and behind, respectively, the supply of product 11, i.e. reservoir 102, while allowing passage only to the front at 19a of a film of product around the movable element 7, in the way of a wringer. The clearance allowed by the lip 19a matches the viscosity of the product. The discharge and the spread of the product 3 on the surface of the movable element 7 can be performed through capillarity. The movable element 7 can be mounted by snap connection in the supply space 11, i.e. in the housing 110.

In order to simplify the design, it can be preferred that product can pass between the movable element 7 and the bottom of the supply 11, here the wall 21.

Additionally, the device is provided with a housing 15 which can form a push handle in which is accommodated the light source 9 to which is preferably movably secured a capsule 17 comprising a supply 11 of product and the movable element 7. This can simplify the use of a single use capsule 17 which then becomes a disposable, which can be disposed of after use.

Hence, capsules can be exchanged or replaced and therefore especially provide several products to be applied, or diffuse several rays, for instance while having various movable elements 7. Diffusing several rays shall be understood as including the possibility of changing the color of light passing through the capsule due to differences in refraction indexes, coloring of the ball 7 or the housing, providing refraction elements such as but not limited to Fresnel lenses or prisms or similar means for influencing the light.

In this way, the capsules 17 become replaceable, especially disposable, refills, so that the use of one-time doses of products such as different serums, is made possible. The reservoir 102 of a capsule 17 can for example hold a small amount of product 3 to be dispensed, which can for example be less than 10 ml, more specifically less than 5 ml, more in particular less than 3 ml, such as for example between 0.01 and 1.5 ml. Other volumes are obviously possible.

The supply 11, i.e. the reservoir 102 is provided in a body 110 of the capsule relative to which the applicator element 7 is movable.

Between the light source 9 and the movable element 7 is interposed a first wall 21, transparent to the ray which it allows to pass, towards the movable element. In particular in FIG. 1, the wall 21 is perpendicular to the axis 13, as e.g. shown in FIG. 1.

It is recommended that this wall 21 be transparent to a wavelength of between 400 nm and 1400 nm, preferably such that, it substantially does not alter the optical characteristics of the radiation and/or that it has a size and shape sufficiently great for a ray to concentrate on a defined focal point depending on the product and the desired effect (FIG. 6). Alternatively the wall 21 may have (an) opening(s) or window(s) for allowing the ray(s) to pass through.

Preferably, the transparent wall 21 is secured to or an integral part of the capsule 17 such that it is airtight to the product, thus giving this wall a double function. The light source 9 will then be in a zone isolated from the product contained in the supply 11 i.e reservoir 102.

Figure 2:
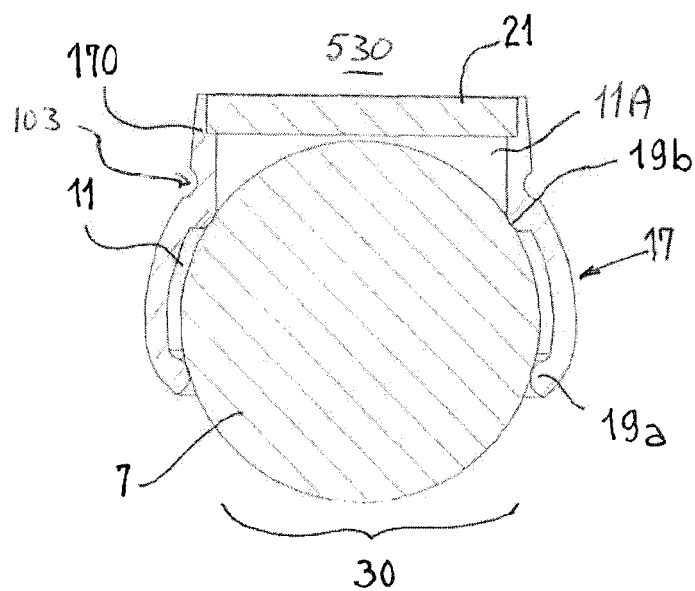

To simplify assembly and disassembly and reduce the production cost of the two assemblies, the housing 15 and the capsule 17 can be snapped together through the lip 150 of the housing elastically retaining the rear top piece 170, via the peripheral groove 103, in the housing where also the transparent wall 21 is engaged. The lip 150 and groove 103 can form first and second connecting means or elements 100, 101. This is advantageous for assembly/disassembly in case only the capsule 17 is utilized. In FIGS. 1, 2 it is indicated that the linking means 150 of the capsule, in this example preferably formed by this peripheral groove 103 of the body 110, are situated towards the closed wall 21, laterally relative thereto, and therefore do not hinder the passing of the ray.

Figure 3:
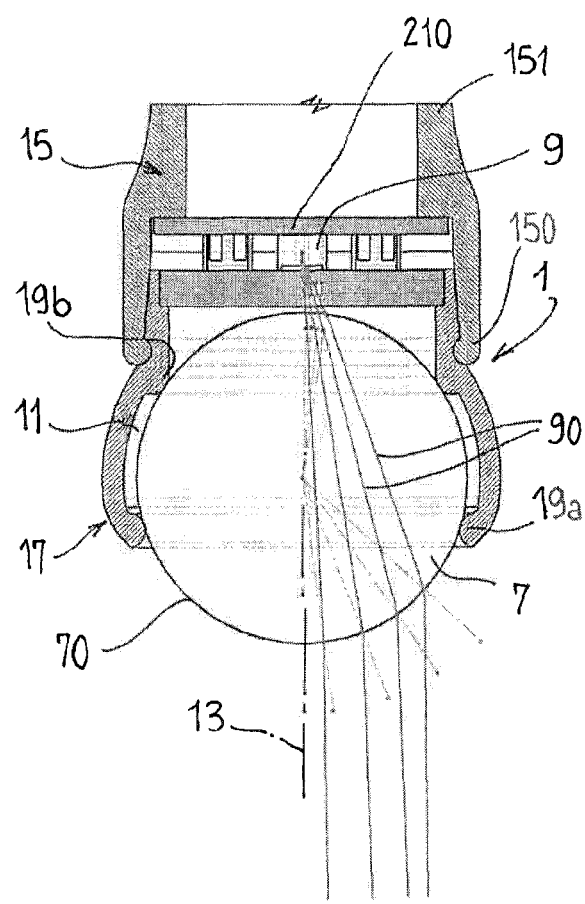

Further to the rear, especially illustrated in FIG. 3, in the housing 15, the light source 9 may be protected by a second wall 210, which may or may not be transparent to the ray from the light source 9 and secured to the inside of this housing 15.

With the capsule 17 and housing 15 in assembled condition, the second wall 210 is situated opposite the first wall 21.

Thus, the light source 9 is interposed between the first and the second wall 21, 210.

The two walls 21, 210 can be parallel to each other. The ray emitted by the light source 9 at a predetermined wavelength and which is emitted as far as the application surface 5, travels successively through the first wall 21, the applicator means 7, then the layer of product 3 discharged on the surface 30, each having its own refraction index.

Advantageously, the applicator means 7 defines an optical system. This can be hollow, with air in the interior, or any substance in solid, liquid or gaseous form, so that the focal point can be placed anywhere one wants at the exit of the capsule.

For a good hold and easy handling after application of the product, it is advised that the housing 15 comprises or forms a push handle or casing 151 for moving the movable element. Advantageously, this push handle extends in a direction, here 131, towards the movable element/applicator means 7.

In the housing 15, in the push handle or casing 151 are disposed one or several electrical feed batteries 27 of the light source 9 or a connector to a mains.

Incidentally, for safety of use and long lasting functioning, it is recommended that the movable element 7 be mounted to or engaging a first element 29 of the device 1 which, in turn, is movably mounted for translation following an axis relative to a second element 31 of the device. The above-mentioned axis can be the axis 13 that passes through the source 9 and the movable element 7.

It is thus ensured that the starting means 47, started here, apart from the distribution zone 30, by the intermediary of the movable element 7, allow the start of the emission of the ray by the light source, while at the same time the product is applied through this distribution zone, such that the flow of light then passes through the applied product.

The fact is that the first element 29, bearing the movable element 7, is favorably mounted for translation between:
a first position (FIG. 4) where the first and second element 29, 31 are axially distanced from each other while opening (interrupting) an electric circuit comprising the light source 9 which, then, cannot emit the ray, and a second position (FIG. 5), where, by the pressure of the movable element 7 on the surface 5, along axis 13, the first and second element 29, 31 are axially brought together while closing the electrical circuit such that then, the light source emits, preferably automatically, the ray 90.

It is preferred that a biased element 33 is provided between the first and second element 29, 31, to return them in a natural way to the first position, as is illustrated.

The first and second element 29, 31 are electrically conducive to form the interrupter 35 which is opened when the device 1 is in rest (the circuit comprising the light source 9 does not emit any light) and closed if a pressure according to the axis 13 is applied thereon (typically through a contact with the application surface 5). The light can be emitted in the movable element 7 with a slight delay controlled by an electronic decade of 39 (circuit delay FIG. 1), all this for security reasons.

What is thus prevented is that the light source emits a strong light to the eyes of the user.

Figure 4:
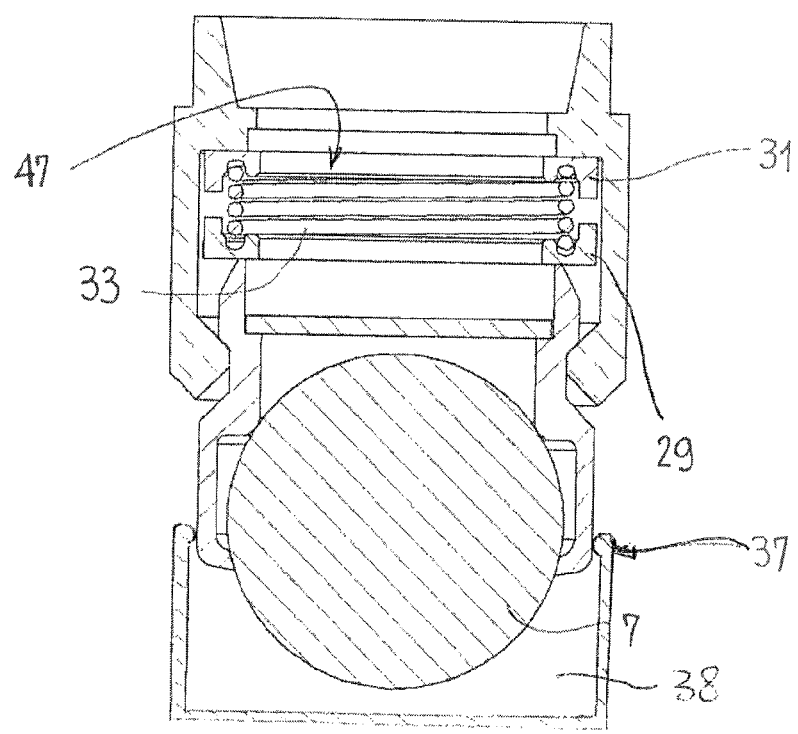
Figure 5:
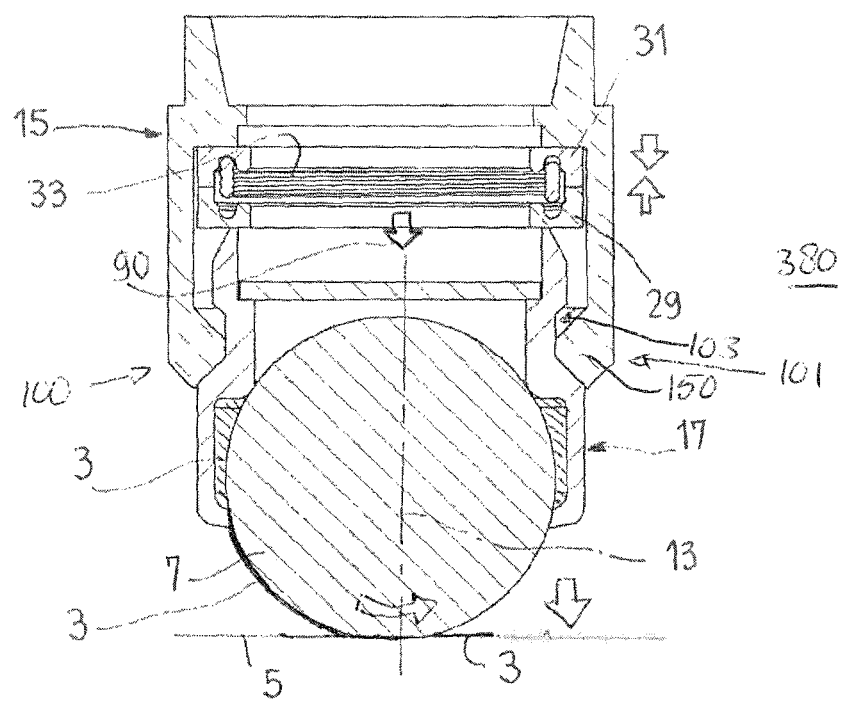

Alternatively the first and second coupling means 100, 101 of the capsule 17 and housing 15 are designed such that once the capsule 17 is properly coupled to the housing 15 the elements 29, 31 are brought into the conductive position, such as e.g. shown in FIG. 5, and only after removal of the capsule 17 from the housing 15 the electrical circuit will be broken, as e.g. shown in FIG. 4. An advantage thereof can be that the movable element 7, i.e. the ball, can also be moved lightly over the surface, still emitting light.

Preferably, a lid 37, advantageously opaque, and therefor in turn an anti-ray protection, covers the product supply 11 and is removably secured to the body of the device, preferably to the capsule 17. Mounted on the capsule 17, the lid 37 may or may not bear on the movable element 7 that it covers here. Preferably, it is robustly secured so as to prevent (or at least limit) the passage of air towards the internal volume 38 which it isolates, beneath it. Before the first opening of the lid 37, the air pressure in volume 38 can be lower relative to the exterior 380, or filled with an antioxidant substance aiming to keep the product 3 from oxidizing or limit oxidation.

Connecting it to a one-dose capsule 17 is particularly appropriate.

To adapt the device in particular to various types of application surfaces, for instance skin, it is provided that the light source 9 can generate different wavelengths, alternatively or simultaneously during a continuous contact between the movable element 7 and the surface 5.

During such a phase of, at the same time, discharge of the product 3 on this surface and illumination thereof by the light emitted by the light source 9, the generated light beam can be modulated in intensity or sequence during contact.

As already indicated, the reservoir or supply 11 can extend between the movable element 7 and the light source 9. This would then imply that the refraction index of the product 3 should be taken into account. The product 3 to be spread then forms an integral part of the optical system, its refraction index being taken into account in the optical sum.

However, this is not advantageous if the quantity of the stored product 3 in the device, especially the capsule is reduced, the more so as one risks less uniform (or non-uniform) distribution of the product 3. Furthermore, restricting the amount of product 3 in the radial periphery of the supply 11, transversely to the axis 13, could allow for omission of the rear wall 21.

Advantageously, the movable element 7 has such dimensions that, for optimal application on the skin, it can travel on all parts of the face, in particular also around the eyes. In a preferred embodiment, through rotation generated by friction on the dermis, the movable element 7 applies the product a priori obtained by capillarity from the reservoir 11.

In FIGS. 7-11 is shown a device 1 where, by mechanical deformation of the hollow piece 49 mounted in the housing 15, it is possible to axially (axis 13) separate this housing and the capsule 17. To this end, movable brackets 51a, 51b are borne laterally by the deformable part 40 and are mounted pivotally or deformably relative thereto. An internal passage 490 passes along the axis 13 all through the deformable piece 49. This internal passage provides, parallel to the pivotal axes 510a, 510b, lateral bearing surfaces 53a, 53b which are diametrically opposed relative to each other and accessible to the user on the housing, perpendicular to the axis 13. Thus, by pressing on these bearing surfaces, the hollow piece 49 is deformed transversely to the direction of pressing, and to the axis 13 and thus the brackets 51a, 51b are pivoted from a position naturally apart from each other along the direction of deformation to a position closer together so that the capsule 17 can be secured and/or removed relative from the housing.

Figure 7:
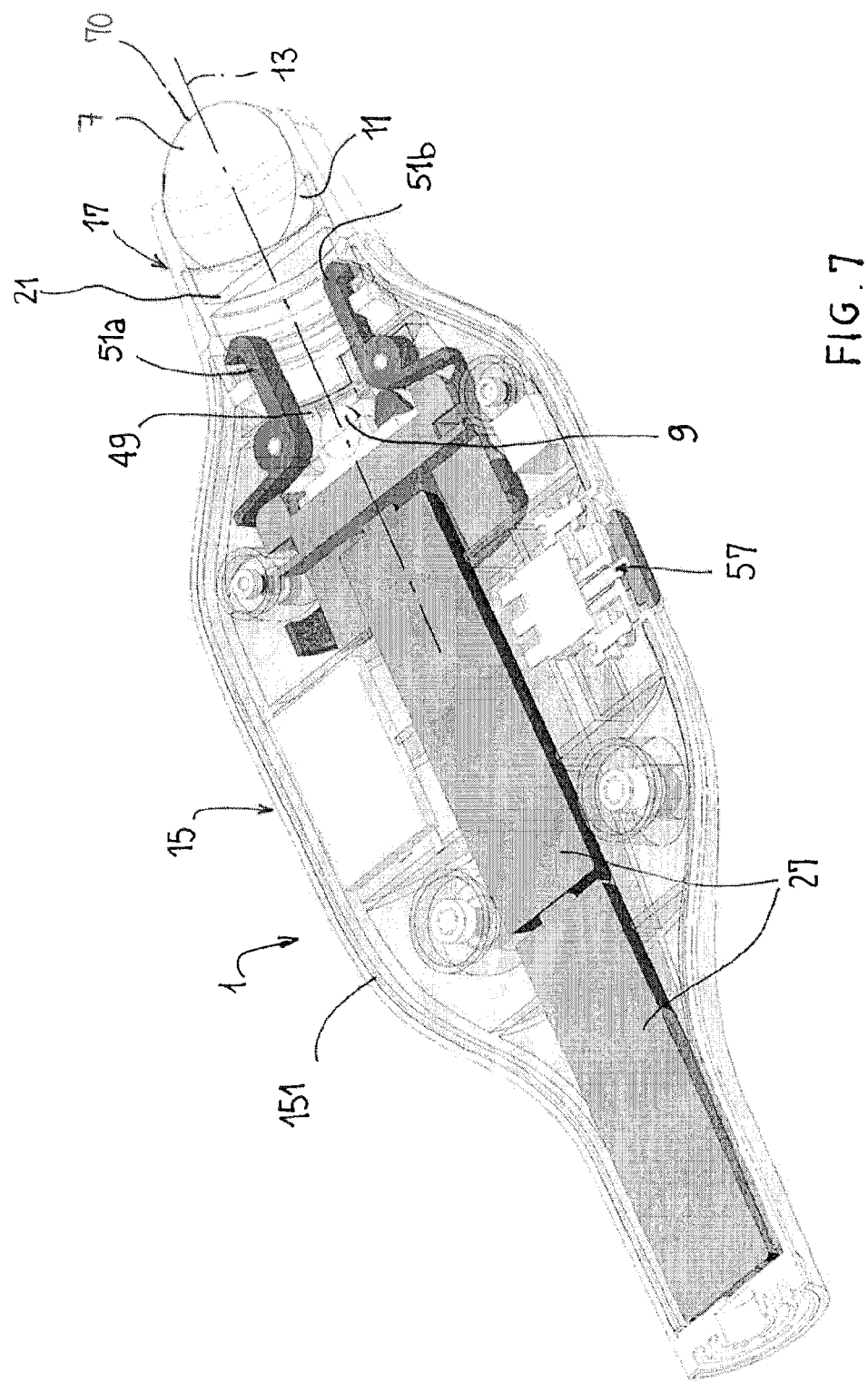
Figure 8:
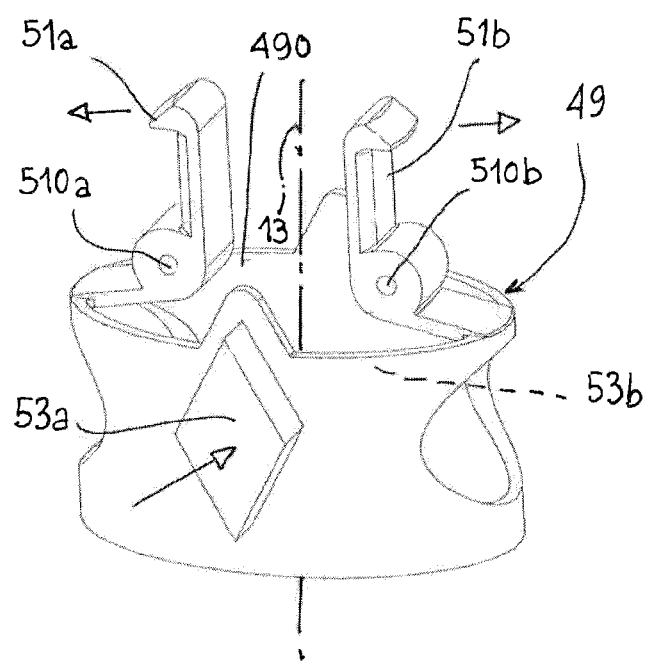

Additionally, as is shown in particular in FIGS. 7, 8, the capsule 17 comprises linking means 52, forming first coupling means 100, for ensuring the desired removable fixation between the capsule 17 and the second linking means 54, forming second coupling means 101, of the housing 15, the first and second linking means being situated at a distance from the zone of passage of the light ray coming from the light source 9 and passing to the product application zone 70.

More specifically, the capsule encloses a cavity 53 which:
is open at one side towards the outside at 530 (opposite the movable element 7),
has a wall 21 that separates it from the supply 11, and
comprises a side 55 around an opening of the cavity 53, the side belonging to the first linking means 52 or first coupling means 100, so that there are removably received the movable brackets 51, which belong to the second linking means 54 or second coupling means 101.

Figure 11:
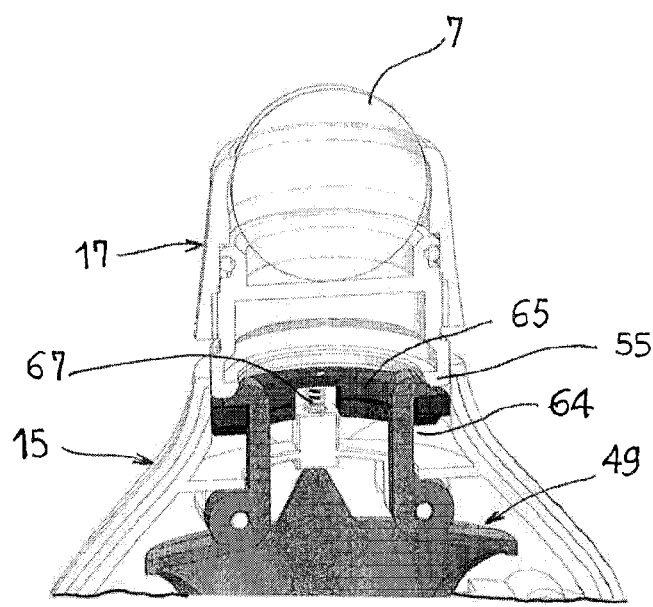

To improve the engagement of the side 55 which is annular here, under the end 511a, 511b curved towards the interior of the brackets 51a, 51b, these latter provide biased inclinations with complementary inclinations at the inside periphery of the side (see FIG. 11 for the guiding of the inclinations which effects the brackets 52 to approach one another).

Figure 9:
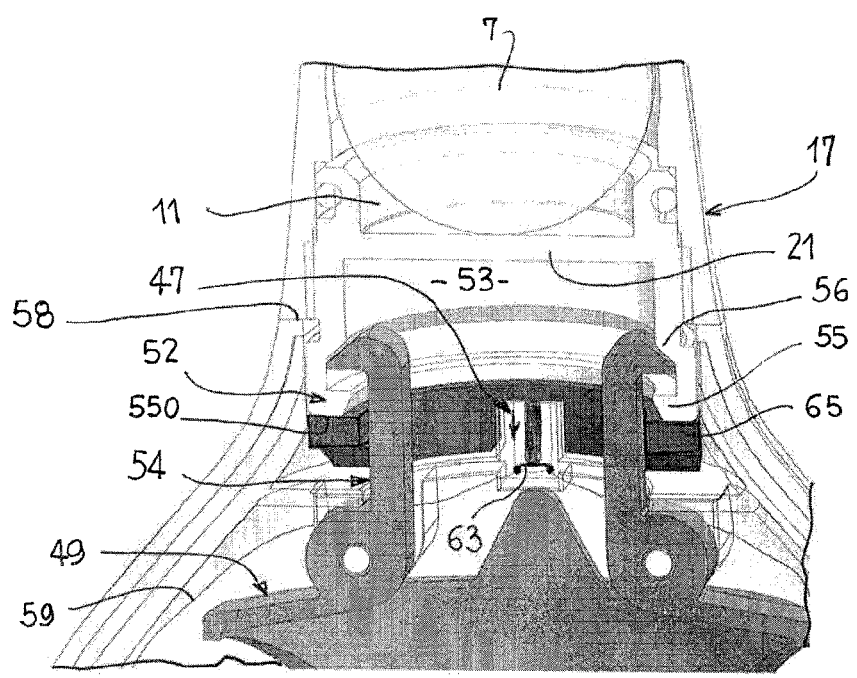
FIGS. 9, 10 and 11 show enlarged zones of the device of FIG. 7 in interior view.
Figure 10:
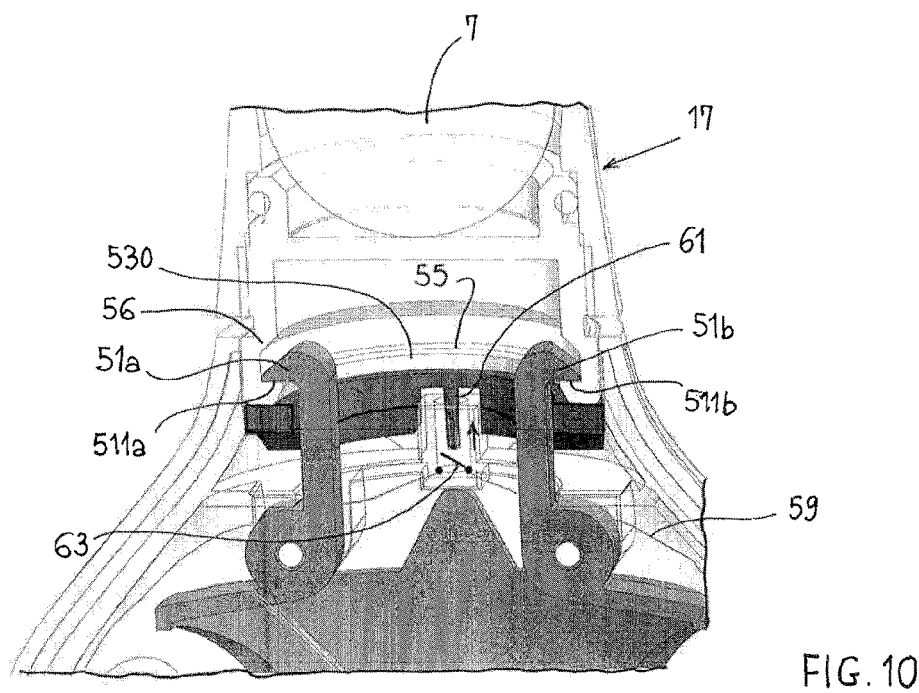

In FIGS. 7, 9, 10, it can be seen that with the capsule 17 secured in the housing, the starting means 47, 58 enable the start of the emission of the ray(s) by the light source 9, while it should be specified that the solution of FIGS. 1-5 favorably comprises a means 57 comprising an on/off interrupter which is at all times accessible to the user from the outside of the housing. The interrupter 57 is connected to the light emitter 9 so that the light emission is started at the closure of the interrupter.

If, now, in FIGS. 7, 9, 10, the starting means 47 is actuated as before by the pressure of the movable element 7 on a support, via the surface 70, it is preferred that this means 57 also comprises the interrupter 63 on/off accessible from the outside of the housing 15.

With regard to the functioning of the starting means 47, if this 57 is in "go" position, it is provided, with the capsule 17 is secured to the housing, this capsule has once more the capacity to move relative to the housing 15, through a displacement (translation) according to the axis 13, for:

c) in a first position (FIG. 10), opening the electric circuit 59 which comprises the light source 9 and the battery 27, and d) in a second position (FIG. 9), closing the electric circuit, so that the light source can then emit light ray(s).

Thereto, a mechanical action can be chosen, on an internal interrupter 63, of a foot 61 connected to a ring 65 which is held in the opening 64 of the housing through which pass the brackets 51a, 51b, in the direction of the capsule.

Under the effect of the displacement of the capsule 17, according to the axis 13, produced by the pressure of the movable element 7, the ring 65 comes to press on the internal interrupter 63, via the projecting foot 61.

As can be seen in FIG. 9, preferably, an outside wall 550 of the capsule (here the base of the side 55) presses on the ring 65.

To secure the whole, the housing is furthermore provided with biasing means 67, such as springs, which return the capsule in a natural way to the first position, the interrupter open (FIGS. 10, 11). Thus, pressure on the internal interrupter 63 produced by the axial pressure of the movable element 7 will act against the stiffness of the biasing means 67.

Thus, the capsule 17 can move along the axis 13 relative to the housing.

Here, the guiding and one of the axial stop means are provided through lateral brackets 51a 51b which are located parallel to the axis 13.

Engaged in a groove formed perpendicularly to the axis 13, between the annular side 55 and an interior shoulder 56, the lateral brackets move there over a short axial distance. Preferably, also an annular exterior stop means 58 for the housing/capsule is provided.

With respect to the aspect "impact" on the surface 5 of a living body of the distribution of the product 3, together with the transmission of light towards this surface, it should be noted that the object is to achieve photo bio-modulation. What is involved here is stimulation through a row of photons (along the emitted wavelengths). For the skin it is recommended that it penetrates as far as the level of the dermis, or the hypodermis, the cells of the dermic matrix and in particular fibroblasts responsible for the production of collagen and blood vessels (collagen being the principal component of the skin, in particular responsible for its firmness and tonicity.) The stimulation of the blood circulation provides for an optimal feed of oxygen and nutriments to the cells for an improved functioning thereof.

Preferably, the radiation of the source 9 towards this surface 5 comprises infrared rays, a source of warmth.

As to active substances, in particular the following are provided:

ACS III, with molecular formula C37H69NO5,

INIC: Dipalmitol Hydroxyproline

Collagen synthesis enhancer Type III

An active ingredient for (human) skin care, which selectively enhances the synthesis of the isotope III of collagen A "transporter" liposome containing dipalmitate hydroxyproline covered by hydroxyl proline which acts as a modulator of the phenotypical expression of the fibroblast.

Collatein

An induction of HSP 47 accelerates the extracellular transport of the pro-collagen III and the folding of the alpha chains of the collagen during the synthesis of collagen and its externalization before the extracellular fibrillogenesis.

HSP 47 which are chaperone proteins specific for the synthesis of collagen.

In the context of a therapeutic treatment or a cosmetic indication of product 3, together with the emission of the precited rays, it is clear from what precedes that preferably, conditions for use are as follows the product is applied on the skin, via the distribution zone 30 of the device, and preferably simultaneously, a light radiation is emitted towards the skin, at the location of this distribution zone, while a focal point is used such that a photo bio-modulation is created that penetrates as far as the dermis, or as far as the hypodermis, the cells of the dermic matrix and in particular the fibroblasts responsible for the production of collagen and the blood vessels.

In the preceding examples, the distribution zone of product is limited to the surface of the applicator element 7. But, as is already mentioned, it can be provided that the light energy transmitted by the source 9, via for instance a series of electroluminescent diodes can pass sideways and in particular around the applicator element 7 before it reaches the surface 5. In this case, all or a part of the light energy will not pass through the applicator element 7, nor more generally the application means of the product, as they are. The important thing is that the energy, produced here in the form of (a) light wave(s), arrives on or in the surface 5 on which the product 3 has been applied.

It is clear that although the distribution (therefore the spread) of the product on the surface 5 is performed by the movable element 7, if, as is preferred, such an element is present also. The application of the product on the surface can be performed in another way, for instance by an associated distributor, separate from the device 1.

Thus, whatever the embodiment, a product containing an active component or forming a cosmetic product is distributed on a surface 5 of a living body, where it is activated, preferably simultaneously with its application, by the transmission to the cells situated on or in this surface of at least one wavelength in the form of a ray of energy.

FIG. 12 shows schematically in perspective view a device 1 according the disclosure, for dispensing a product and light, as discussed, in cross section along a mid sectional plane including the longitudinal axis 13. The device 1 comprises, as in the further embodiments as shown, a housing 15 and a capsule 17. The capsule 17 comprises again a ball 7 as applicator element, rotatably mounted in a capsule body 110, such that the ball 7 can rotate substantially freely in all directions. The capsule 17 comprises at least first coupling or linking means 100, for cooperation with second coupling or linking means 101 provided in and/or on the housing 15, as will be discussed further. By the first and second coupling or linking means 100, 101 the capsule 17 can releasably be coupled to the housing 15. The first and second coupling or linking means could as discussed with respect to FIG. 1-11, or as discussed hereafter.

In FIG. 12 the casing cq housing 15 is shown, in cross section, showing schematically part of the interior, including an active applicator unit 104, and a capsule 17. Further parts, such as batteries and circuitry for operating the device, as discussed before, are not shown for convenience sake. In FIG. 13-15 basically embodiments of the applicator unit 104 and a capsule are shown, which can be fitted in the casing or housing 15.

FIG. 12A shows schematically, in cross section, part of an active applicator unit 104 and a capsule 17, showing a general concept of active dispensing and light guiding. In FIG. 12A the ball 7 is shown, held by housing 110, such that it can rotate in all directions. Part of the ball 7 at a first side 105 of the housing 110 extends outside the housing 110, and can be brought into contact with a surface onto which product has to be supplied. At an opposite side the housing 110 is provided with a chamber or reservoir 102 for product 3. The reservoir 102 comprises a peripheral wall 106, preferably substantially cylindrical, defining an open end 107 opposite the ball 7. Between the ball 7 and the reservoir 102 a wall 21 is provided, with a relatively small opening 108 connecting the reservoir 102 with the space 11B around the ball 7. In the chamber or reservoir 102 a piston 109 is provided, sealing against the peripheral wall 106 in a known manner, for example by an O-ring or flexible sealing lip or the like, such that the piston 109 can be moved within the chamber or reservoir 102 towards the opening 108, along the axis 13. Initially the reservoir 102 will be filled with product 3 to be dispensed, preferably substantially entirely. The size of the opening 108 may be chosen, depending on for example the viscosity of the product, such that under atmospheric pressure at least at room temperature, for example between 18 and 30° C. or even higher temperatures, the product will be contained within the reservoir 102, even if held up side down, i.e. with the opening 108 facing downward.

When in such capsule 17 the piston 109 is moved towards the opening 108, product will be forced through the opening 108 and against the ball 7, in a volume equal to about the frontal surface area of the piston times the displacement along the axis 13, and thus well defined and controllable. If the ball 7 is pressed against the opening 108, the opening 108 may even be better sealed for keeping the product 3 inside the reservoir, for example prior to use of the capsule, whereas the ball can be pushed off the opening 108 by the product when the piston is pushed towards the opening 108. The ball 7 can for example be pressed against the opening 108 prior to use by a cap 37.

In embodiments the ball 7 can be held in the housing 110 without seals closing a space between part of the ball surface and the housing 110. In embodiments the housing 110 can comprise a substantially bowl shaped holding part 110A, having an upper rim 19 spaced apart over a small gap 115 from the ball surface, as shown in FIGS. 12B and C. To this end the rim 19 may be provided with a series of small, spaced apart notches 19C or the like, for defining the gap 115 and at the same time keeping the ball rotatably closed in the housing 110. This can have the advantage that once the product is picked up by the ball 7 it will not be scraped off by a seal. Thus even small amounts of product dispensed at a time will almost entirely be transferred to the surface 5 to be treated.

In the general embodiment of FIG. 12A the capsule 17 is pressed in an axial direction along the axis 13 into the housing 15. In the housing 15 a push rod 111 is provided, driven by any suitable means (not shown in FIG. 12A) such as but not limited to an electrical, pneumatic, hydraulic or magnetic motor, stepping motor, or by hand, for example by a screw knob external to the housing. The push rod 111 engages the side of the piston 109 facing outward from the reservoir 102, through the open end 107, preferably fitting into an indentation 112 in the piston, in order to properly center the piston and push rod. One or more light guides 113 can be positioned around the wall 106 of the reservoir, extending between a position close to the light source 9, here shown as a plurality of LED's 9A, and a position closed to or in abutment with the housing 110 of the capsule 17. Thus light from the light source 9, especially the LED's can be transferred to the capsule 17 by the light guide(s) passed the reservoir 102, unhindered by the product 3 in the reservoir 102, as shown by the arrows 90.

As can be seen in FIG. 12A the capsule 17 can be provided with a groove or cutouts 103, similar to the groove 103 shown in e.g. FIG. 1-5, for example at the transition between the part 110A and the peripheral wall 106 or below it, in which the light guide(s) 113 can hook, similar to the rim 150 of FIG. 1 or the fingers 52 in FIG. 6-11, for holding the capsule 17 in position and at the same time providing a proper placing of the ends 116 of the light guide(s) close to or in abutment with the housing 110 of the capsule 17. The light guides(s) can be resiliently flexible or can be mounted such that they can move partly outward in order to mount and release the cartridge 17 again. For example the light guide(s) can tilt, bend or translate to that end.

As can be seen in FIG. 12A a spring 117 can be provided below the cartridge, which can be loaded by placing the cartridge and/or by moving the piston 109 and rod 111 forward, such that at least when the piston 109 is near or at an end position, with the reservoir substantially empty, and the capsule 17 is released by the coupling means such as the light guide(s), the capsule is pushed out of the housing by the spring 117, at least in part, such that it can be more easily removed, for example by tilting the device 1 above a waste basket or the like, such that a user has to have no or only minimal contact with the used capsule.

FIG. 12 shows part of a casing or housing 15, with a applicator unit 104 carrying a capsule 17 with a cap 37, prior to use for dispensing. In this embodiment the unit 104 is represented with a cartridge similar to that of FIG. 12A and the unit 104 as such as shown in more detail in FIG. 13. In this embodiment the push rod 111 comprises a hollow cylinder 120 engaging the piston 109, and a rod portion 121 mounted on a spindle 122 of a motor 123. Within the cylinder 120 a spring 124 is provided, biasing the cylinder 120 away from the rod portion 121. The rod portion 121 is provided with two wing portions 125 extending side ways and sliding along sliding surfaces 126 in the casing 15, such that the rod portion 121 is prevented from rotation around the axis 13 and around the spindle 122. The rod portion is provided with internal screw threads 127 complementary to screw threads 128 on the spindle. Thus a rotation of the spindle 122 driven by the motor 123 in the right direction will axially move the rod portion and thus the push rod 111 as such, pushing the piston 109 into the reservoir 102. The spring 124 is resilient such that the piston 109 can be pushed up to against the wall 21, emptying the reservoir substantially completely. However, when the piston 109 has been moved into the end position the rod portion 121 can be moved slightly further in order to load the spring 124, such that when the capsule 17 is released it is pushed out by the spring 124.

Again upon placing the capsule 17 a switch can be operated for empowering the device, especially the light source 9 and/or the motor 123.

The general concept of a device 1 of FIG. 12 is also used in the embodiments shown in FIG. 13-15, be it with different constructions.

FIG. 13A shows in perspective view a device 1 in cross section, of which the capsule 17 is as discussed with reference to FIG. 12. In this embodiment however the coupling means between the capsule 17 and the housing 15 are arranged differently. In this embodiment the housing 15 or at least the unit 104 comprises an arm 129 pivotably mounted. The arm 129 has a hook 130 which can fit in a groove 103 in the capsule 17, especially near the transition between the wall 106 and the housing part 110A. The arm is biased by a spring 131, such that the hook 130 is forced into said groove 103. The opposite end 132 of the arm 129 can be pushed, such that the hook 130 is pivoted out of the groove 103. Then the capsule 17 can be released out of the housing 15, and as discussed before, be pushed out by the spring 124.

In FIG. 13A a cap 37 is mounted on the capsule 17, over the ball 7, wherein the cap 37 comprises, at a side facing the ball 7 a rim 38A forcing the ball 7 against the opening 108, especially against a sealing ring 108 around the opening 108. Thus the opening 108 is closed by the ball 7 as long as the cap 37 is mounted.

Figure 13D:
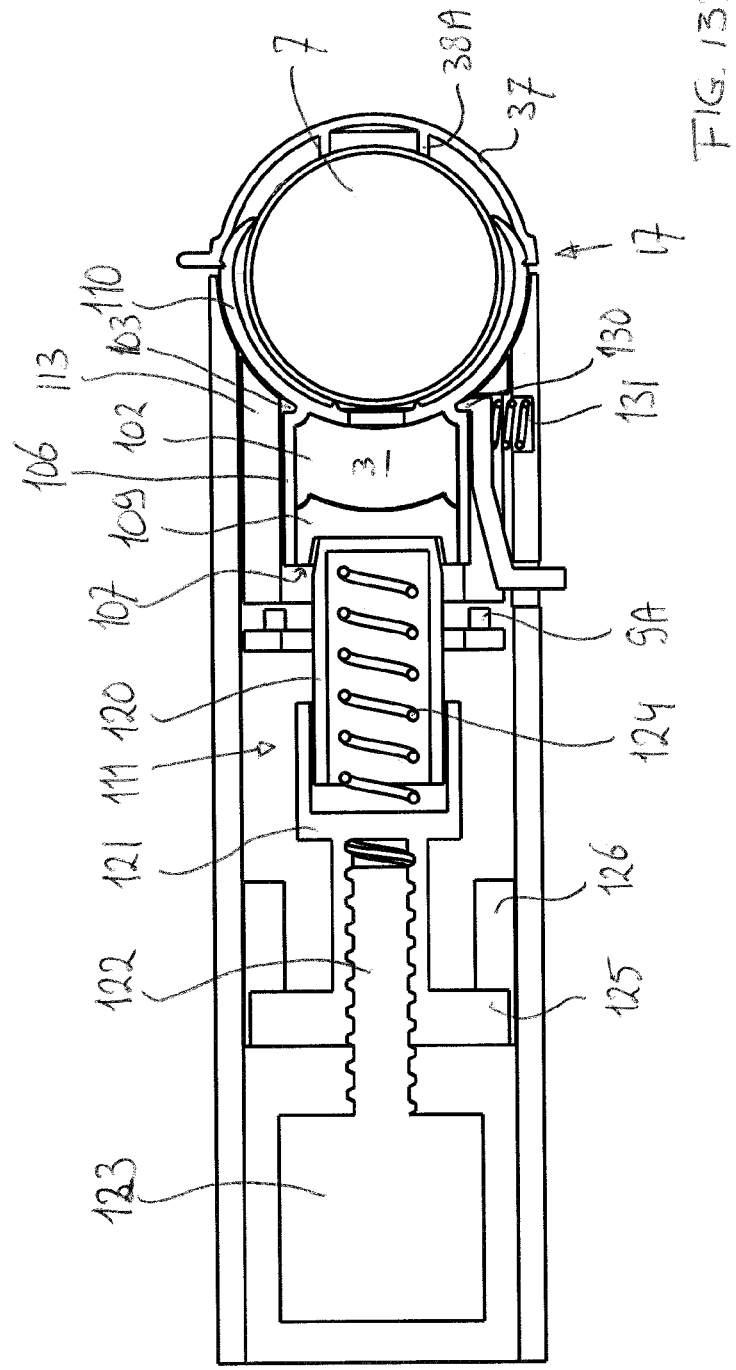

In the embodiment of FIG. 13 (which includes all of FIGS. 13A-H) the piston 109 has a face facing the opening 108 which is adapted to fit snugly against the wall 21, in order to minimize a rest volume of the reservoir 102 when the piston 109 is moved forward against the wall 21.

FIG. 13B-I shows a sequence of placing a capsule 17, dispensing the product 3 and removing the capsule 17 again. In FIG. 13B-I only the unit 104 and capsule 17 are shown.

FIG. 13B shows the rod portion 121 in a rearward end position (i.e. closest to the motor 123) and the capsule 17 with cap 37 held close to the inserting opening 15A of the housing 15 or at least of the unit 114. The piston 109 is also in the most rearward position, the volume of the reservoir 102 maximal. FIG. 13C shows the capsule during insertion into the opening 15A, the hook 130 sliding along the wall 106, biased against the wall 106 by the spring 131. In FIG. 13D the capsule 17 has been inserted maximally, such that the hook 130 can engage the groove 103, locking the capsule 17 in position. The rod 111 engages the piston 109, specially the indentation 112 therein. Then the cap 37 can be removed, as shown in FIG. 13E. Then the device 1 is ready for use.

By driving the motor 123 the piston is moved forward, dispensing the product 3 from the reservoir 102.

Figure 13I:
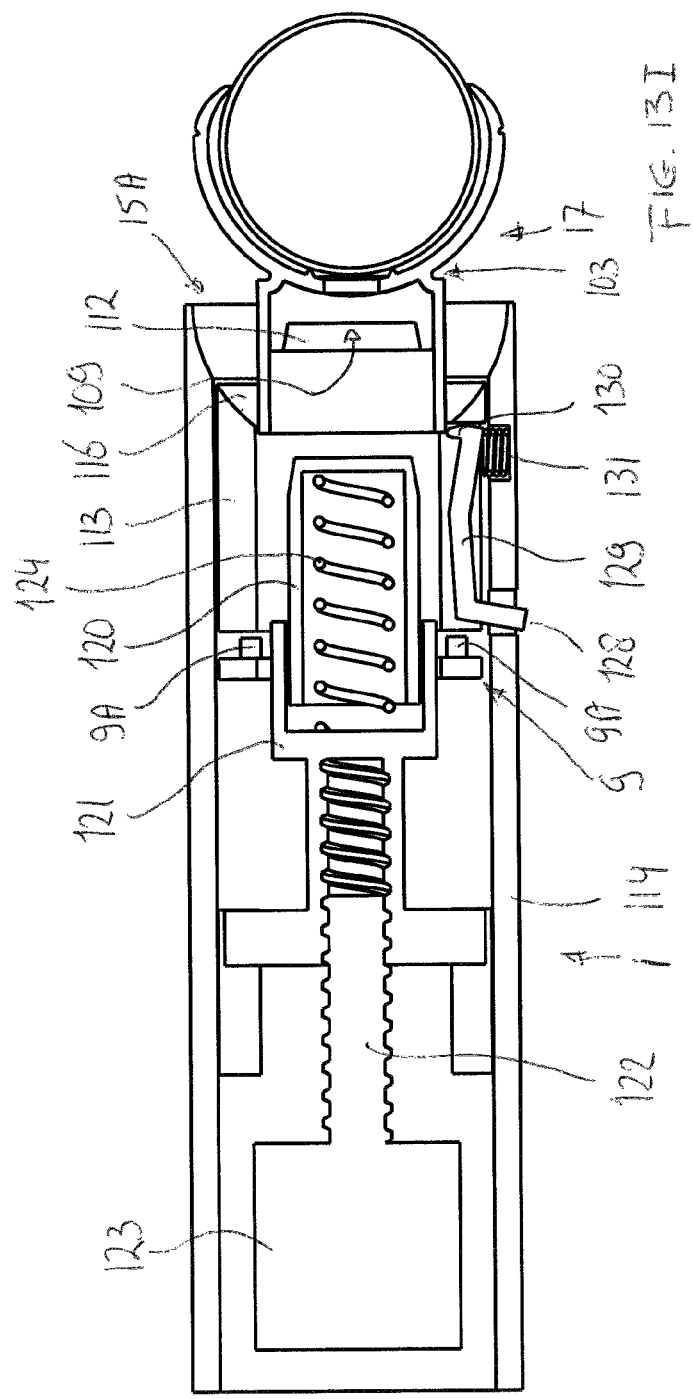

FIG. 13F shows the unit 104 with the capsule 17, with the piston 109 moved forward maximal by the motor, the reservoir empty. Then in FIG. 13G the motor 123 has been driven slightly further, such that the spindle 122 has moved the rod portion further forward, loading the spring 124. Then in FIG. 13H the arm is shown pivoted such that the hook 130 is pulled out of the groove 103, thus releasing the capsule 17. Thus the capsule 17 is pushed out of the housing 15 by the spring 124, as shown in FIG. 13I.

In FIG. 13 the light is guided through the light guides 113 alongside the reservoir 102 to the capsule 17, to be radiated out through the ball 7.

FIG. 14A shows an alternative embodiment of a unit 104 and capsule 17, in cross sectional perspective view, wherein the capsule again is substantially as shown and discussed in FIGS. 12 and 13. One difference is in a groove 103A in an outward facing side of the wall 106. In this embodiment the unit 104 has, as in the embodiments of FIGS. 12 and 13, a substantially cylindrical housing part 104A with a first end 104B forming the insertion opening 15A. In this embodiment the push rod 111 is substantially solid, with a bore containing internal screw threads 127 for cooperation with screw threads 128 on the spindle 122. Within the housing 104A, close to the first end 104B a guide element 133 is provided for receiving the capsule 17 or at least the reservoir 102 thereof. The guide element 133 can for example be substantially cylindrical, and has a ring shaped cross wall 134 with an opening 135 through which the push rod 111 can extend for engaging the piston 109. Spaced further apart from the end 104B in the unit 104 a further cross wall 136 is provided, through which the push rod 111 extends as well. A spring 137 is provided between the two cross walls 134 and 136, around the push rod 111. In the wall 138 of the guide element 133 a number of openings 171 is provided, containing each a ball element 139, which in the coupled position as shown in FIG. 14A extend into the groove 103A, locking the capsule inside the guide element 133, since the balls 139 cannot move outward in this position due to the wall of the unit 104.

As can be seen in FIG. 14A the wall 138 comprises a further opening 140, for example at a side of the cross wall 134 opposite the ball elements 139, into which a hook 130 of an arm 129 can engage when the guide element 133 has been pushed into the housing 104 maximally. The arm 129 is pivotally mounted in the wall of the unit 104, biased by a spring 141 such that the hook 130 is forced into the opening 140, locking the guide element 133 in position. In this position the spring 137 is loaded, biasing the guide element 133 and thus the capsule 17 outward of the housing 15, 104, in axial direction.

In an inward facing side of the wall of the housing 104A a groove 143 is provided, such that if the guide unit 133 is moved outward the balls 39 can move outward into the groove 143, releasing the capsule 17 from the guide element 133. Thus the capsule can be removed again.

In FIG. 14 (including all FIGS. 14A-I) the light source 9, such as LED's 9A can be provided for example at the cross wall 136, at least one light guide 113 being provided by or in the guide element 133. A switch 144 can be provided within the unit 104, such that the guide element 133 can operate the switch when being pushed into the housing 15. This switch 144 can thus switch the electrical circuit, for example the motor and/or the light source, such that if the capsule is not placed properly, the device or at least the light source 9 cannot be activated.

FIG. 14B shows a unit 104 with a capsule 17 spaced apart from the unit 104. As in the embodiment of FIG. 13 a cap 37 is placed over the ball 7, pushing the ball against the rim 108A closing the opening 108. In the housing 104A the guide element 133 is moved outward towards the end 104B, such that the balls 139 are received in the groove 143, such that the capsule 17 can be pushed into the guide element 133. The rod 111 is in a rearward position, the spring 137 relatively relaxed.

In FIG. 14C the reservoir of the capsule 17 is received in the guide element 133, such that an end thereof abuts the cross wall 134. In FIG. 14D the capsule 17 and guide element 133 are shown pushed further in, along the axis 13. Since the groove 143 has an inclined surface the balls 139 will be taken along with the guide element 133 and forced inward, into the groove 103A in the capsule 17, thus locking the capsule in the guide element 133. As is shown in FIG. 14D the arm 129 is pushed outward, such that the guide element 133 can pass to the position shown in FIG. 14E in which the hook 130 is pushed back, into the opening 140, locking the guide element 133 in this position. The spring 137 has been compressed and thus loaded. The switch 144 has been operated such that the device can be used. The push rod 111 engages the piston 109.

In FIG. 14F the push rod 111 and piston 109 are show in a position moved maximally forward by the motor 123 and spindle 122, such that the piston 109 engages the wall 21. Thus the reservoir has been emptied, the product 3 dispensed therefrom. If in this position the arm 129 is engaged, such that the hook 130 is pulled out of the opening 140, as is shown in FIG. 14G, the spring 137 will push the guide element 133 back outward to the end 104B, such that the balls 139 can move back into the groove 143, as shown in FIG. 14H. From this position the capsule 17 can be taken out of the guide element 133 and thus out of the housing 15, as shown in FIG. 14I.

The device 1 according to the disclosure can comprise a control unit 146, preferably connected to the motor 123, the light source 9 and/or a switch operated by placing the capsule 17 as discussed. The control unit can for example be programmed to operate the motor 123 such that the piston 109 is driven forward into the reservoir for dispensing the product. The motor 123 can for example be driven such that the piston is driven forward intermittently, in steps, such that the product is dispensed in a number of quantities, for example equal portions, in a number of steps each having a predetermined duration. For example the control can be set to dispense $1/n^{th}$ of the volume of product 3 from the reservoir every X seconds, such that in n steps of X seconds all of the product is dispensed, whereas during each period the ball 7 can be rolled over the surface 5 for applying the product over a different portion of said surface. For example n could be between 1 and 50, for example between 4 and 20, such as for example between 8 and 15. In an test example n was chosen to be 12, whereas the duration X of each period was chosen to be 15 seconds. Thus all of the product 3 was dispensed in twelve periods of 15 seconds each. However, the duration of the period and/or the number of steps can be chosen as desired. In an embodiment the control unit 145 can be provided with the possibility to choose between different dispensing regimes or to set the number of steps and/or the duration thereof by a user.

The invention claimed is:

1. A method for applying product and light to a surface for non-medical treatment of said surface, wherein a capsule comprising a reservoir containing a product is releasably coupled to a housing comprising at least a light source and a control unit, wherein the capsule comprises a movable element such as a ball onto which product from the reservoir can be fed for dispensing it to a surface by the ball, wherein light is transmitted from the light source through the capsule to the surface prior to, during and/or after dispensing said product onto said surface, whereafter the capsule is removed from the housing and replaced by another capsule.

2. A method according to claim 1, wherein the housing further comprises a drive element and the reservoir comprises a movable and/or deformable wall, wherein for dispensing the product from the reservoir the drive element is driven, controlled by the control unit, and wherein the drive element is driven intermittently, such that the product is dispensed in a series of volumes.

3. A device for distributing, on a surface of a living body, a product containing an active component for forming a cosmetic product, and the release/discharge, at least as far as this surface, of energy in the form of a light wave, the device comprising:
 a distribution zone of product on said surface; and
 at least one light source emitting at least one light ray towards the surface,
 wherein the device comprises a housing and a capsule releasably coupled to the housing,
 wherein the capsule comprises a reservoir containing the product and a movable element forming at least part of the distribution zone,
 wherein the reservoir has at least one moveable and/or deformable wall, such as a piston, such that a volume of the reservoir can be reduced for dispensing the product, by moving and/or deforming said at least one wall, and
 wherein the housing comprises the at least one light source.

4. A device according to claim 3, wherein the movable element has an exterior side for applying product on said surface,
 wherein the movable element is an ovoid form enabling the application of the product,
 wherein the movable element pivots about at least one pivotal axis, and the external wall of the movable element is outwardly convex, and
 wherein the movable element is traversed by the light rays and/or passed by the light ray.

5. A device according to claim 3, wherein the housing is provided with a drive element for said moving and/or deforming of said at least one wall.

6. A device according to claim 3, wherein the capsule is at least partly transparent to the light from the light source, for allowing the light to pass into and through the capsule, to be transferred to the surface.

7. A device according to claim 3, wherein the volume of the reservoir can be reduced by the movable and/or deformable wall to about 0 ml.

8. A device according to claim 4, wherein the reservoir is positioned at a first side of the movable element and the distribution zone is provided at an opposite side of the movable element,
 wherein an opening is provided for allowing product to pass from the reservoir towards the movable element, and
 wherein the opening has a side such that the product will substantially only leave the reservoir through the opening when pressurized by the movable and/or deformable wall.

9. A device according to claim 3, wherein the device comprises at least one light guide for guiding light from the light source, such as one or more LED's, in the direction of the distribution zone.

10. A device according to claim 3, wherein the device comprises at least one light guide for guiding light in the housing from the light source, such as one or more LED's, to the capsule,
 wherein the capsule is at least partly transparent for said light, such that the light can pass into and through the capsule to a surface, and
 wherein the at least one light guide extends past an outside of the reservoir.

11. A device according to claim 3, wherein the reservoir contains less than 10 ml of product.

12. A device according to claim 3, wherein the capsule has a longitudinal axis and comprises a housing with a bowl shaped housing part and a reservoir extending outward from said bowl shaped housing part, the bowl shaped housing part housing the movable element,
 wherein the reservoir has a peripheral wall and part of the bowl shaped housing part extends radially outward from the peripheral wall, relative to the axis,
 wherein the bowl shaped housing part rests against an end of the housing of the device, when the reservoir has been introduced into the housing of the device, and
 wherein coupling means are provided in the housing for engaging coupling means of the capsule for locking the capsule relative to the housing.

13. A device according to claim 3, wherein the device comprises a control unit for controlling at least the light source.

14. A device according to claim 3, wherein the device comprises a control unit for controlling at least the light source and a drive element for deforming and/or moving the deformable and/or movable wall.

15. A device according to claim 14, wherein the control unit is programmed to drive the drive element such that the product is dispensed from the reservoir in a series of intermittent steps.

16. A device according to claim 14, wherein a switch is coupled to the control unit, wherein the switch is positioned such that it is activated by coupling the capsule to the housing of the device and deactivated when removing the capsule, wherein the light source can only emit light when the switch is activated.

17. A device according to claim 16, wherein the switch comprises:
 a first body mounted with the movable element and itself movably mounted for translation along an axis relative to a second body of the device, between:
  a first position wherein the first and second body are axially distanced one from the other while opening an electric circuit comprising the light source which thus cannot emit light, and
  a second position wherein, through the pressure of the movable element along said axis, the first and second body are axially brought closer together while closing the electric circuit so that the light source emits the ray; and
 a biasing means disposed between the first and second body for returning them in a natural manner to the first position.

18. A device according to claim 3, wherein the movable element that provides the product distribution zone, and/or a supply which feeds the movable element with product, define an optical device such that, with the movable element in contact with said surface of a body, the passage of optical rays in the device concentrate these rays in a contact zone, or a few millimeters beyond, so that then, if an application surface is the skin, the focal point is located in the dermis or at most between the dermis and the epidermis.

19. A device according to claim 3, comprising a first wall at least partly transparent for light emitted by the light source, interposed between the light source and the distribution zone and allowing passage of the light to the distribution zone.

20. A capsule for use in a device according to claim 3.

21. A capsule according to claim 20, wherein the capsule comprises a ball rotatably mounted in a housing, wherein the housing comprises a reservoir having a movable and/or deformable wall, for containing product to be dispensed by the ball, and wherein the reservoir is in communication with a space between the ball and the housing through at least one opening, wherein the opening is relatively small, and wherein the reservoir has a volume for a relatively small amount of product.

22. A device according to claim 3, wherein the movable element is a ball.

23. A capsule for distributing, on a surface of a living body, a product containing an active component or forming a cosmetic product, the capsule having a product distribution zone and comprising:
 in a body, a reservoir comprising a supply of product which is in communication with the product distribution zone, and
 first linking means for removably securing the capsule to second linking means of a housing in which is disposed a light source,
 the capsule comprising a movable element in the form of a ball, forming at least part of the distribution zone; and
 wherein the reservoir has at least one moveable and/or deformable wall in the form of a piston, such that the volume of the reservoir can be reduced for dispensing the product, by moving and/or deforming said at least one wall.

24. A capsule according to claim 23, wherein the first and second linking means are situated at a distance from the light ray coming from the light source.

25. A capsule according to claim 23, the capsule is at least partly transparent, for allowing the light from the light source to pass into and through the capsule, to be transferred to the surface.

26. A capsule according to claim 25, the capsule comprising a cavity which is open on one side towards the exterior, has a blind flange which isolates the supply of product, and the first linking means are situated towards this blind flange, laterally relative thereto.

27. A capsule according to claim 23, comprising a lid disposed for isolating the supply of product from the outside, while covering a space where there is an atmosphere directed to protect, prior to the first opening of the lid, the product from oxidation.

28. A capsule according to claim 23, wherein the capsule is disposable.

29. A capsule according to claim 23, wherein the movable element is a ball.

30. A product distribution device containing an active component for distribution on a surface of a living body and the radiation towards this surface, the device comprising:
 a distribution capsule according to claim 23, and
 a housing to which the capsule is secured in a removable manner, by first and second linking means, and in which is disposed the light source adapted for emitting said light ray towards the product distribution zone.

31. A device according to claim 30, wherein the light source emits the rays through the movable element.

32. A device according to claim 30, where, at the outside, the movable element comprises the distribution zone and this movable element is configured for concentrating the ray on or a few millimeters beyond said distribution zone, which is a contact zone with the surface of the body such that then, with the distribution surface being the skin, the focal point can be situated in the dermis or, at most, between the dermis the epidermis.

33. A device according to claim 30, wherein, with the capsule secured to the housing, the housing comprises a push handle for moving the movable element, the push handle extending in a direction towards this element and the light source, and wherein are disposed feed batteries or a battery for the light source.

34. A device according to claim 30, wherein, with the capsule secured to the housing, starting means, activatable by the user, at a distance from the distribution zone and/or by the movable element, allow the start of the emission of the light ray by the light source simultaneously with the distribution of the product via this distribution zone, such that the flow of light passes through the discharged product.

* * * * *